United States Patent
Soderlind et al.

(10) Patent No.: US 7,432,083 B2
(45) Date of Patent: *Oct. 7, 2008

(54) METHOD FOR IN VITRO MOLECULAR EVOLUTION OF PROTEIN FUNCTION

(75) Inventors: Ulf Hans Eskil Soderlind, Lund (SE); Carl Arne Krister Borrebaeck, Lund (SE)

(73) Assignee: Bioinvent International AB, Lund (SE)

( * ) Notice: Subject to any disclaimer, the term of this patent is extended or adjusted under 35 U.S.C. 154(b) by 358 days.

This patent is subject to a terminal disclaimer.

(21) Appl. No.: 11/109,264

(22) Filed: Apr. 19, 2005

(65) Prior Publication Data

US 2005/0266451 A1    Dec. 1, 2005

Related U.S. Application Data

(63) Continuation of application No. 10/118,100, filed on Apr. 8, 2002, now Pat. No. 6,989,250, which is a continuation of application No. 09/341,711, filed as application No. PCT/GB98/00219 on Jan. 26, 1998, now abandoned.

(30) Foreign Application Priority Data

Jan. 24, 1997   (GB)   ................................. 9701425.2

(51) Int. Cl.
*C12P 19/34* (2006.01)
*C12Q 1/68* (2006.01)
*G01N 33/00* (2006.01)
*C07H 21/02* (2006.01)
*C07H 21/04* (2006.01)

(52) U.S. Cl. .................. 435/91.2; 435/6; 435/91.1; 436/94; 536/23.1; 536/24.3; 536/24.33

(58) Field of Classification Search ............ 435/6, 435/91.1, 91.2, 91.51, 455, 463, 465; 436/94; 536/23.1, 24.3, 24.33, 25.3
See application file for complete search history.

(56) References Cited

U.S. PATENT DOCUMENTS

| | | | |
|---|---|---|---|
| 5,023,171 A | 6/1991 | Ho et al. | |
| 5,252,479 A | 10/1993 | Srivastava | |
| 5,395,750 A | 3/1995 | Dillon et al. | |
| 5,573,907 A | 11/1996 | Carrino et al. | |
| 5,605,793 A | 2/1997 | Stemmer | |
| 5,811,238 A | 9/1998 | Stemmer et al. | |
| 5,830,721 A | 11/1998 | Stemmer et al. | |
| 5,834,252 A | 11/1998 | Stemmer et al. | |
| 5,837,458 A | 11/1998 | Minshull et al. | |
| 5,969,108 A | 10/1999 | McCafferty et al. | |
| 6,159,690 A | 12/2000 | Borrebaeck et al. | |
| 6,300,064 B1 | 10/2001 | Knappik et al. | |
| 6,335,160 B1 * | 1/2002 | Patten et al. ................ | 435/6 |
| 6,989,250 B2 * | 1/2006 | Soderlind et al. ........... | 435/91.2 |

FOREIGN PATENT DOCUMENTS

| | | |
|---|---|---|
| EP | 0 368 684 A1 | 5/1990 |
| EP | 0 415 731 A2 | 3/1991 |
| EP | 0 456 304 A1 | 11/1991 |
| EP | 0557897 | 9/1993 |
| EP | 0 911 396 A2 | 4/1999 |
| EP | 0 934 999 A1 | 8/1999 |
| GB | 9701425.2 | 1/1997 |
| JP | 6-121696 | 5/1994 |
| JP | 2001-519643 | 10/2001 |
| WO | WO 90/07936 | 7/1990 |
| WO | WO 92/01047 | 1/1992 |
| WO | WO 92/07075 | 4/1992 |
| WO | WO 92/15702 | 9/1992 |
| WO | WO 93/07282 | 4/1993 |
| WO | 94/03627 | 2/1994 |
| WO | WO 94/12632 | 6/1994 |
| WO | 94/18219 | 8/1994 |
| WO | WO 95/22625 | 8/1995 |
| WO | 96/07754 | 3/1996 |
| WO | WO 96/17056 | 6/1996 |
| WO | WO 96/23873 | 8/1996 |
| WO | WO 97/08320 | 3/1997 |
| WO | WO 97/20078 | 6/1997 |
| WO | 98/15567 | 4/1998 |
| WO | WO 98/27230 | 6/1998 |
| WO | WO 98/32845 | 7/1998 |
| WO | WO 98/42832 | 10/1998 |
| WO | WO 98/58080 | 12/1998 |
| WO | 95/22615 | 5/2008 |

OTHER PUBLICATIONS

Definition for "complematarity determining region" from Wikipedia, the free encyclopedia. Printed on Jun. 11, 2008.*

(Continued)

*Primary Examiner*—Frank W Lu
(74) *Attorney, Agent, or Firm*—Dann, Dorfman, Herrell & Skillman; Robert C. Netter; Kathleen D. Rigaut

(57) ABSTRACT

The present invention relates to a method for in vitro creation of molecular libraries evolution of protein function. Particularly, it relates to variability and modification of protein function by shuffling polynucleotide sequence segments. A protein of desired characteristics can be obtained by incorporating variant peptide regions (variant motifs) into defined peptide regions (scaffold sequence). The variant motifs can be obtained from parent DNA which has been subjected to mutagenesis to create a plurality of differently mutated derivatives thereof or they can be obtained from in vivo sequences. These variant motifs can then be incorporated into a scaffold sequence and the resulting coded protein screened for desired characteristics. This method is ideally used for obtaining antibodies with desired characteristics by isolating individual CDR DNA sequences and incorporating them into a scaffold which may, for example, be from a totally different antibody.

34 Claims, 10 Drawing Sheets

OTHER PUBLICATIONS

Definition for "single chain variable fragment" from Wikipedia, the free encyclopedia. Printed on Jun. 11, 2008.*

Alber, T. et al. "Contributions of hydrogen bonds of Thr 157 to the thermodynamic stability of phage T4 lysozyme"; Nature 330: 41-46 (1987).

Arrizubieta, M.J. et al. "Increased Thermal Resistance and Modification of the Catalytic Properties of a â-Glucosidase by Random Mutagenesis and in Vitro Recombination"; J. Biol. Chem. 275: 28843-28848 (2000).

Barbas, C.F. et al. "Assembly of combinatorial antibody libraries on phage surfaces: The gene III site"; Proc. Natl. Acad. Sci. USA 88: 7978-7982 (1991).

Barbas, C.F. et al. "Semisynthetic combinatorial antibody libraries: A chemical solution to the diversity problem"; Proc. Natl. Acad. Sci. USA 89: 4457-4461 (1992).

Boder, E.T. et al. "Yeast surface display for screening combinatorial polypeptide libraries"; Nature Biotechnol. 15: 553-557 (1997).

Boublik, Y. et al. "Eukaryotic Virus Display: Engineering the Major Surface Glycoprotein of the *Autographa californica* Nuclear Polyhedrosis Virus (AcNPV) for the Presentation of Foreign Proteins on the Virus Surface"; Biotechnol 13: 1079-1084 (1995).

Brown; Molecular Biology LabFax, BIOS Scientific Publishers Ltd., Oxford, 154 (1991).

Bucholz, C.J. et al. "In vivo selection of protease cleavage sites from retrovirus display libraries"; Nature Biotechnol 16: 951-954 (1998).

Casson, L. P. et al. "Evaluation of Loss and Change of Specificity Resulting from Random Mutagenesis of an Antibody $V_H$ Region"; J. Immunol. 155(12): 5647-5654 (1995).

Chang, C.J. et al. "Evolution of a cytokine using DNA family shuffling"; Nature Biotechnol. 17: 793-797 (1999).

Christians, F.C. et al. "Directed evolution of thymidine kinase for AZT phosphorylation using DNA family shuffling"; Nature Biotechnol. 17: 259-264 (1999).

Crameri, A. et al. "Combinatorial Multiple Cassette Mutagenesis Creates All the Permutations of Mutant and Wild-Type Sequences"; BioTechniques 18: 194-196 (1995).

Crameri, A. et al. "Molecular evolution of an arsenate detoxification pathway by DNA shuffling"; Nature Biotechnol. 15: 436-438 (1997).

Crameri, A. et al. "DNA shuffling of a family of genes from diverse species accelerates directed evolution"; Nature 391: 288-291 (1998).

Deng, S. et al. "Simultaneous randomization of antibody CDRs by a synthetic ligase chain reaction strategy"; Nucleic Acids Research 21(18): 4418-4419 (1993).

Dower, W.J. et al. "High efficiency transformation of *E. coli* by high voltage electroporation"; Nucleic Acids Research 16(13): 6127-6145 (1988).

Eckstein, F. et al. "Exogenous application of ribozymes for inhibiting gene expression"; Ciba Found. Symp. 209: 207-212 (1997).

Ernst, W. et al. "Baculovirus surface display: construction and screening of a eukaryotic epitope library"; Nucleic Acids Research 26(7): 1718-1723 (1998).

Fisch, I. et al. "A strategy of exon shuffling for making large peptide repertoires displayed on filamentous bacteriophage"; Proc. Natl. Acad. Sci. USA 93: 7761-7766 (1996).

Grabherr, R. et al. "Expression of Foreign Proteins on the Surface of *Autographa Californica* Nuclear Polyhedrosis Virus"; BioTechniques 22: 730-735 (1997).

Granziero, L. et al. "Baculovirus cDNA libraries for expression cloning of genes encoding cell-surface antigens"; Journal of Immunological Methods 203: 131-139 (1997).

Griffiths, A.D. et al. "Isolation of high affinity human antibodies directly from large synthetic repertoires"; EMBO J. 13: 3245-3260 (1994).

Hanahan, D. "Studies on Transformation of *Escherichia coli* with Plasmids"; J. Mol. Biol. 166: 557-580 (1983).

Higuchi, K. et al. "Cell display library for gene cloning of variable regions of human antibodies to hepatitis B surface antigen"; Journal of Immunological Methods 202: 193-204 (1997).

Ho, S.N. et al. "Site-directed mutagenesis by overlap extension using the polymerase chain reaction"; Gene 77: 51-59 (1989).

Hoogenboom, H. et al. "By-passing Immunisation Human Antibodies from Synthetic Repertoires of Germline $V_H$ Gene Segments Rearranged in Vitro"; J. Mol. Biol. 227: 381-388 (1992).

Prickett, K.S. et al. "A Calcium-Dependent Antibody for Identification and Purification of Recombinant Proteins"; BioTechniques 7: 580-589 (1989).

Horton, R.M. et al. "Engineering hybrid genes without the use of restriction enzymes: gene splicing by overlap extension"; Gene 77: 61-68 (1989).

Huse, W.D. et al. "Generation of a Large Combinatorial Library of the Immunoglobulin Repertoire in Phage Lambda"; Science 246: 1275-1281 (1989).

Kikuchi, M. et al. "An effective family shuffling method using single-stranded DNA"; Gene 243: 133-137 (2000).

Kim, Y. et al. "Bacterial Cell Surface Display of an Enzyme Library for Elective Screening of Improved Cellulase Variants"; Appl. Environ. Microbiol. 66:788-793 (2000).

Kobayashi, N. et al. "Analysis of Assembly of Synthetic Antibody Fragments: Expression of Functional scFv with Predefined Specificity"; BioTechniques 23: 500-503 (1997).

Kuipers, O.P. et al. "Improved site-directed mutagenesis method using PCR"; Nucleic Acids Research 19(16): 4558 (1991).

Larrick, J.W. et al. "Rapid Cloning of Rearranged Immunoglobulin Genes from Human Hybridoma Cells Using Mixed Primers and the Polymerase Chain Reaction"; Biochem. Biophys. Res. Com. 160: 1250-1256 (1989).

Leung, D.W. et al. "A Method for Random Mutagenesis of a Defined DNA Segment Using a Modified Polymerase Chain Reaction"; Technique 1: 11-15 (1989).

Lewin, B. "Processing Is Necessary To Produce Some RNAs"; Genes IV, p. 272 (1990).

Lu, T. et al. "Kinetics and mechanism of BAL 31 nuclease action on small substrates and single-stranded DNA"; Biochimica et Biophysica Acta 1251: 125-138 (1995).

Luqmani, Y.A. et al. "Subtraction Hybridization Cloning of RNA Amplified from Different Cell Populations Microdissected from Cryostat Tissue Sections"; Analytical Biochemistry 222: 102-109 (1994).

Marks, J.D. et al. "By-Passing Immunization: Building High Affinity Human Antibodies by Chain Shuffling"; Bio/Technology 10: 779-783 (1992).

McCafferty, J. et al. "Phage antibodies: filamentous phage displaying antibody variable domains"; Nature 348: 552-554 (1990).

Moore, J.C. et al. "Directed evolution of a *para* -nitrobenzyl esterase for aqueous-organic solvents"; Nature Biotechnol. 14: 458-467 (1996).

Mottershead, D. et al. "Baculoviral Display of the Green Fluorescent Protein and Rubella Virus Envelope Proteins"; Biochem. Biophysis. Res. Com. 238: 717-722 (1997).

Orlandi, R. et al. "Cloning immunoglobulin variable domains for expression by the polymerase chain reaction"; Proc. Natl. Acad. Sci. USA 86: 3833-3837 (1989).

Ostermeier, M. et al. "A combinatorial approach to hybrid enzymes independent of DNA homology"; Nature Biotechnol. 17: 1205-1209 (1999).

Parmley, S.F. et al. "Antibody-selectable filamentous fd phage vectors: affinity purification of target genes"; Gene 73: 305-318 (1988).

Roberts, S. et al. "Generation of an antibody with enhanced affinity and specificity for its antigen by protein engineering"; Nature 328: 731-734 (1987).

Schier, R. et al. "Isolation of Picomolar Affinity Anti-c-erbB-2 Single-chain Fv by Molecular Evolution of the Complementarity Determining Regions in the Center of the Antibody Binding Site"; J. Mol. Biol. 263: 551-567 (1996).

Schmidt, E.R. "Exonuclease digestion of chromosomes for in situ hybridization"; Nucl. Acid Research 16: 10381 (1988).

Sock, E. et al. "DNA Replication of human Polyomavirus JC Is Stimulated by NF-1 in Vivo"; Virology 182: 298-308 (1991).

Söderlind, E. et al. "Domain libraries: Synthetic diversity for de novo design of antibody V-regions"; Gene 160: 269-272 (1995).

Stemmer, W.P.C., "Rapid evolution of a protein in vitro by DNA shuffling"; Nature 370: 389-391 (1994).

Stemmer, W.P.C. "DNA shuffling by random fragmentation and reassembly: in vitro recombination for molecular evolution"; Proc. Natl. Acad. Sci. USA 91: 10747-10751 (1994).

Vaish, N.K. et al. "In vitro selection of a purine nucleotide-specific hammerhead-like ribozyme"; Proc. Natl. Acad. Sci. USA 95: 2158-2162 (1998).

Warren, Mark S. et al. "A Rapid Screen of Active Site Mutants in Glycinamide Ribonucleotide Transformylase"; Biochemistry 35: 8855-8862 (1996).

Yang, W. et al. "CDR Walking Mutagenesis for the Affinity Maturation of a Potent Human Anti-HIV-1 Antibody into the Picomolar Range"; J. Mol. Biol. 254: 392-403 (1995).

Zhang, J. et al. "Directed evolution of a fucosidase from a galactosidase by DNA shuffling and screening"; Proc. Natl. Acad. Sci. USA 94: 4504-4509 (1997).

Garrard, L.J., et al., "Selection of anti-IGF-1 Fab from a Fab phage library created by mutagenesis of multiple CDR loops", Gene, vol. 128: p. 103-109 (1993).

Daughtery, B.L., et al., "Polymerase chain reaction facilitates the cloning, CDR-grafting, and rapid expression of a murine monoclonal antibody directed against the CD18 component of leukocyte integrins", Nucleic Acids Research, vol. 19: p. 2471-2476, (1991).

Soderlind, E., et al., "Phage Display Technology in Antibody Engineering: Design of Phagemid Vectors and in vitro Maturation Systems", Immunological Reviews, No. 130: 109-124 (1992).

Ho, S.N., et al., "DNA and Protein Engineering Using the Polymerase Chain Reaction; Splicing by Overlap Extension", DNA & Protein Engineering Techniques, vol. 2: p. 50-55 (1990).

Shi, X., et al., "Rapid PCR Construction of a Gene Containing Lym-1 Antibody Variable Regions", PCR Methods and Applications, vol. 3: p. 46-53 (1993).

Jirholt, P., et al., "Exploiting sequence space: shuffling in vivo formed complementarity determining regions into a master framework", Gene, vol. 215: p. 471-476 (1998).

U.S. Appl. No. 60/041,666, filed Mar. 25, 1997, Frances H. Arnold et al.

U.S. Appl. No. 60/045,211, filed Apr. 30, 1997, Frances H. Arnold et al.

U.S. Appl. No. 60/046,256, filed May 12, 1997, Frances H. Arnold et al.

U.S. Appl. No. 08/905,359, filed Aug. 4, 1997, Frances H. Arnold.

Hayashi, N., et al., "Simultaneous Mutagenesis of Antibody CDR Regions by Overlap Extension and PCR", BioTechniques, vol. 17: p. 310-315 (1994).

Horton, R.M., et al., "Gene Splicing by Overlap Extension", Methods in Enzymology, vol. 217: p. 270-279, (1993).

Horton, R.M., et al., "Gene Splicing by Overlap Extension: Tailor-Made Genes Using the Polymerase Chain Reaction", BioTechniques, vol. 8: p. 528-535, (1990).

Berger, S.L., et al., "Phoenix mutagenesis: one-step reassembly of multiply cleaved plasmids with mixtures of mutant and wild-type fragments," Anal. Biochem., 214:571-579 and cover sheet, (1993).

Hayden, M.S., et al., "Antibody engineering," Curr. Opin. Immunol., 9:201-212, (1997).

Rouwendal, G.J.A., et al., "Simultaneous mutagenesis of multiple sites: application of the ligase chain reaction using PCR products instead of oligonucleotides," "BioFeedback" in Biotechniques, 15(1): 68-76, (8 sheets enclosed) (Jul. 1993).

Alberts, B., et al. "Molecular Biology of the Cell (Second Edition)." New York: Garland Publishing Inc. 539-540 (1989).

Borrebaek, C. Declaration. Executed Jan. 11, 2006, publication date is not available.

Soderlind, E. Declaration. Executed Jan. 7, 2006, publication date is not available.

Sandle, I. Declaration. Executed Jan. 16, 2006, publication date is not available.

Esposito, G., et al. "Phage display of a human antibody against Clostridium tetani toxin." Gene, 148: 167-168 (1994).

Lewin, B., "Genes V." New York: Oxford University Press. 219-227 (1994).

Prodromou, C., et al. "Recursive PCR: a novel technique for total gene synthesis." Protein Engineering, 5(8): 827-829 (1992).

Reese, C.B. "The chemical synthesis of oligo- and polu-nucleotides: a personal commentary." Tetrahedron, 58: 8893-8920 (2002).

Stryer, L. "Biochemistry (Third Edition)." New York: W.H. Freeman and Company. 217-215 & 743 (1988).

Suleyman, S., et al. "Three new cross-reacting idiotopes as markers for the products of two distinct human VH3 genes expressed in the early repertoire" [Abstract only]. Scand. J. Immunol. 40(6): 681-690 (1994).

Tomlinson, I.M., et al. "The Repertoire of Human Germline VH sequences Reveals about Fifty Groups of VH Segments with Different Hypervariable Loops." J. Mol. Bio., 227: 776-798 (1992).

Vaughn, T.J., et al. "Human Antibodies with Sub-nanmolar Affinities Isolated from a Large Non-immunized Phage Display Library." Nature Biotechnol., 14: 309-314 (1996).

* cited by examiner

Fig.5.

|  |  | CDR1 |
|---|---|---|
| CLONE 31 | LAAQPAMAEVQLLESGGGLVQPGGSLRLSCAASGFTF | SRYAMSWVRQAPG |
| CLONE 3  | LAAQPAMAEVQLLESGGGLVQPGGSLRLSCAASGFTF | SGYAMSWVRQAPG |
| CLONE 11 | LAAQPAMAEVQLLESGGGLVQPGGSLRLSCAASGFTF | SSYAMSWVRQAPG |
| ORIGINAL | LAAQPAMAEVQLLESGGGLVQPGGSLRLSCAASGFTF | SSYAMSWVRQAPG |

|  |  | CDR2 |  |
|---|---|---|---|
| CLONE 31 | KGLEWVS | AISGSGGGTHYADSVKGR | FTISRDNSKNTLYLQMNSLRAEDTA |
| CLONE 3  | KGLEWVS | AISGSGGSTHYADSVKGR | FTISRDNSKNTLYLQMNSLRAEDTA |
| CLONE 11 | KGLEWVS | AISGSGGSTHYADSVKGR | FTISRDNSKNTLYLQMNSLRAEDTA |
| ORIGINAL | KGLEWVS | AISGSGGSTYYADSVKGR | FTISRDNSKNTLYLQMNSLRAEDTA |

|  | CDR3 |  |
|---|---|---|
| CLONE 31 | VYYCARIGQF | WGQGTLVTVSSGGGGSGGGGSQ |
| CLONE 3  | VYYCARIGRF | WGQGTLVTVSSGGGGSGGGGSQ |
| CLONE 11 | VYYCARIGQF | WGQGTLVTVSSGGGGSGGGGSQ |
| ORIGINAL | VYYCARIGQF | WGQGTLVTVSSGGGGSGGGGSQ |

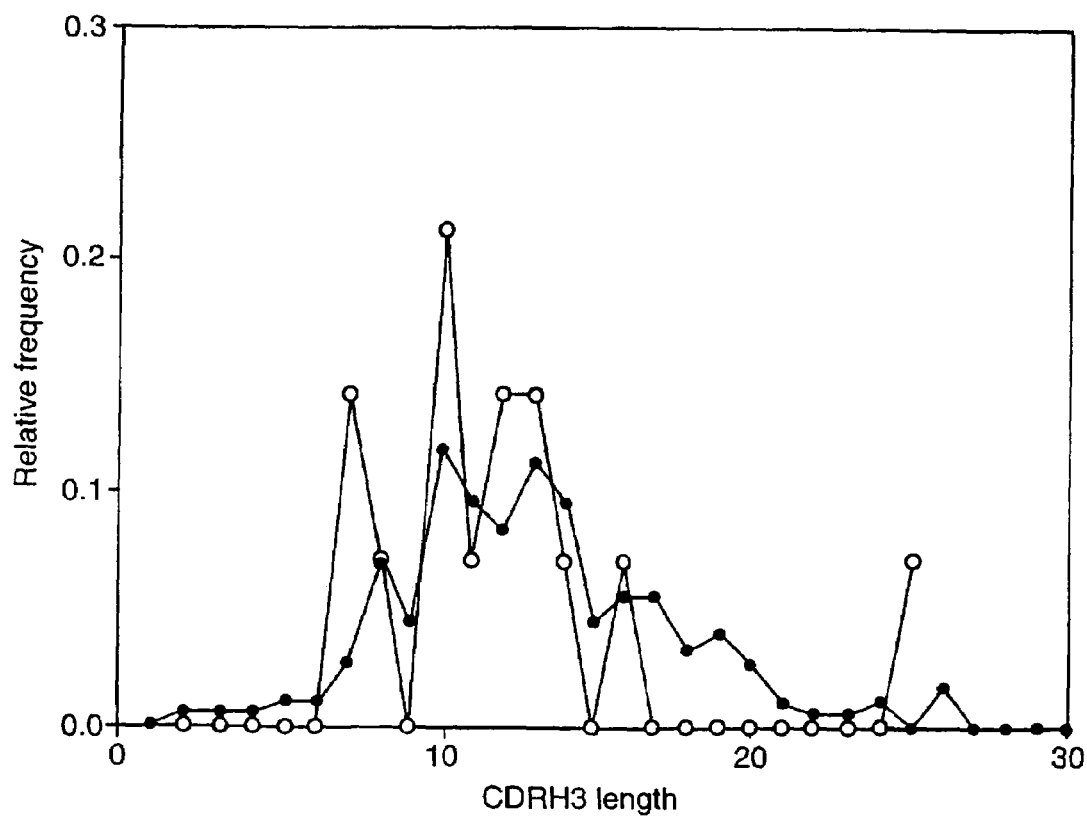

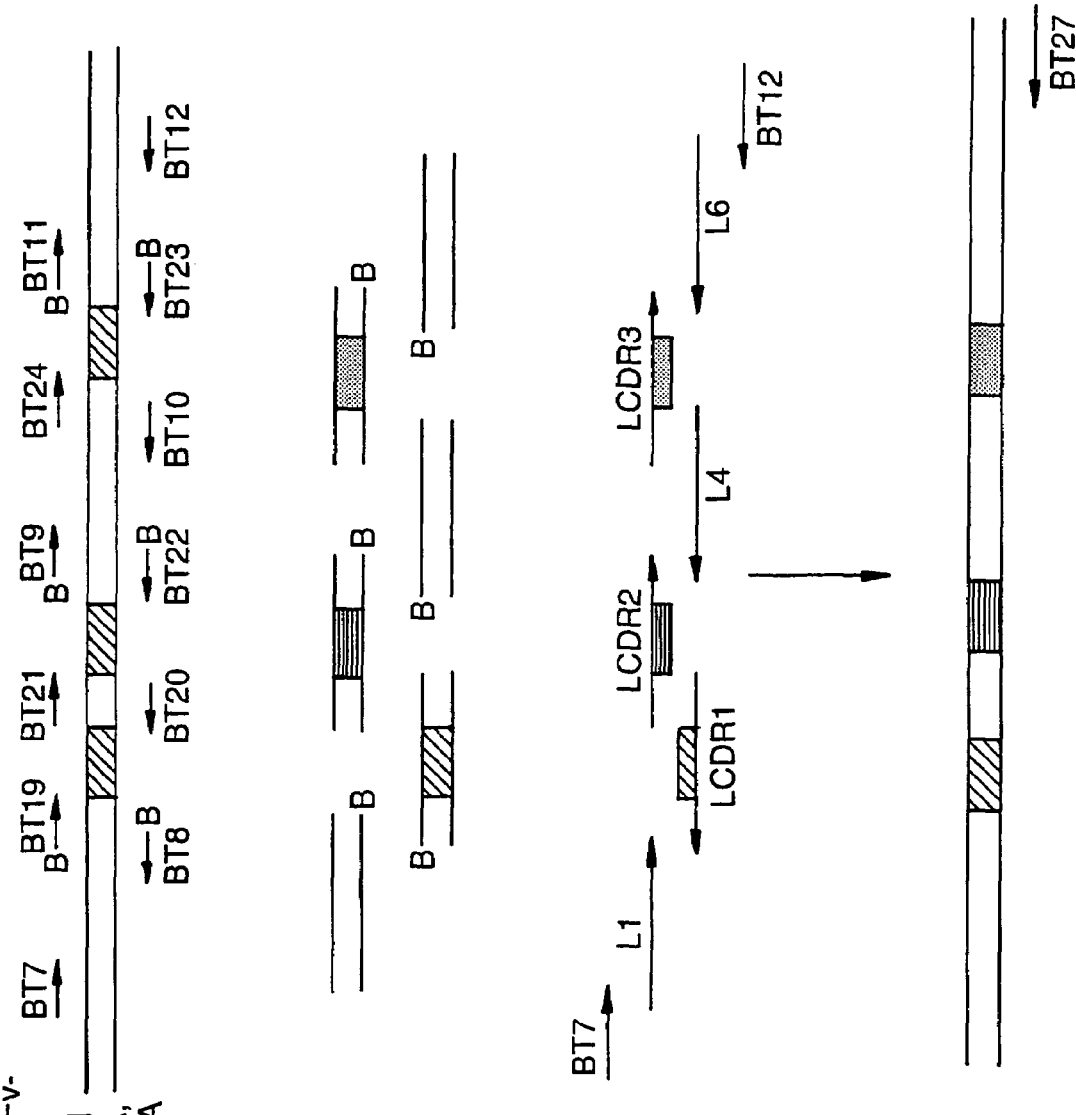

Gel I  Gel II
Gel III  Gel IV

SEQUENCE LISTING

<160> NUMBER OF SEQ ID NOS: 54

<210> SEQ ID NO 1
<211> LENGTH: 40
<212> TYPE: DNA
<213> ORGANISM: Artificial Sequence
<220> FEATURE:
<223> OTHER INFORMATION: Primer

<400> SEQUENCE: 1
gtccctgaga ctctcctgtg cagcctctgg attcaccttt        40

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
tccctggagc ctggcggacc ca                                              22

<210> SEQ ID NO 3
<211> LENGTH: 36
<212> TYPE: DNA
<213> ORGANISM: Artificial Sequence
<220> FEATURE:
<223> OTHER INFORMATION: Primer

<400> SEQUENCE: 3
cgccaggctc cagggaaggg gctggagtgg gtctca                               36

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
ggaattgtct ctggagatgg tgaa                                            24

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
gagccgagga cacggccgtg tattactgtg caaga                                35

<210> SEQ ID NO 6
<211> LENGTH: 35
<212> TYPE: DNA
<213> ORGANISM: Artificial Sequence
<220> FEATURE:
<223> OTHER INFORMATION: Primer

<400> SEQUENCE: 6
gcgctgctca cggtgaccag ggtaccttgg cccca                                35

<210> SEQ ID NO 7
<211> LENGTH: 40
<212> TYPE: DNA
<213> ORGANISM: Artificial Sequence
<220> FEATURE:
<223> OTHER INFORMATION: Primer

<400> SEQUENCE: 7
agcgtctggg accccegggc agagggtcac catctcttgt                           40

<210> SEQ ID NO 8
<211> LENGTH: 28
<212> TYPE: DNA
<213> ORGANISM: Artificial Sequence
<220> FEATURE:
<223> OTHER INFORMATION: Primer -continued

```
<400> SEQUENCE: 8
gggccgttcc tgggagctgc tggtacca                                      28

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
gctcccagga acggccccca aactcctcat ctat                               34

<210> SEQ ID NO 10
<211> LENGTH: 32
<212> TYPE: DNA
<213> ORGANISM: Artificial Sequence
<220> FEATURE:
<223> OTHER INFORMATION: Primer

<400> SEQUENCE: 10
gacttggagc cagagaatcg gtcagggacc cc                                 32

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
ctccggtccg aggatgaggc tgattattac tgt                                33

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
cgtcagcttg gttcctccgc cgaa                                          24

<210> SEQ ID NO 13
<211> LENGTH: 52
<212> TYPE: DNA
<213> ORGANISM: Artificial Sequence
<220> FEATURE:
<223> OTHER INFORMATION: Primer

<400> SEQUENCE: 13
ccgccggatc cacctccgcc tgaaccgcct ccaccgctgc tcacggtgac ca           52

<210> SEQ ID NO 14
<211> LENGTH: 41
<212> TYPE: DNA
<213> ORGANISM: Artificial Sequence
<220> FEATURE:
<223> OTHER INFORMATION: Primer

<400> SEQUENCE: 14
gaccgatgga cctttggtac cggcgctgct cacggtgacc a                       41

<210> SEQ ID NO 15
<211> LENGTH: 66
```

```
<212> TYPE: DNA
<213> ORGANISM: Artificial Sequence
<220> FEATURE:
<223> OTHER INFORMATION: Primer

<400> SEQUENCE: 15
gaggtgcagc tgttggagtc tgggggaggc ttggtacagc ctgggggtc cctgagactc    60 tcctgt                                                              66

<210> SEQ ID NO 16
<211> LENGTH: 72
<212> TYPE: DNA
<213> ORGANISM: Artificial Sequence
<220> FEATURE:
<223> OTHER INFORMATION: Primer

<400> SEQUENCE: 16
ggccgtgtcc tcggctctca ggctgttcat ttgcagatac agcgtgttct tggaattgtc    60
tctggagatg gt                                                       72

<210> SEQ ID NO 17
<211> LENGTH: 43
<212> TYPE: DNA
<213> ORGANISM: Artificial Sequence
<220> FEATURE:
<223> OTHER INFORMATION: Primer

<400> SEQUENCE: 17
cagtctgtgc tgactcagcc accctcagcg tctgggaccc ccg                     43

<210> SEQ ID NO 18
<211> LENGTH: 59
<212> TYPE: DNA
<213> ORGANISM: Artificial Sequence
<220> FEATURE:
<223> OTHER INFORMATION: Primer

<400> SEQUENCE: 18
actagttgga ctagccacag tccgtggttg acctaggacc gtcagcttgg ttcctccgc     59

<210> SEQ ID NO 19
<211> LENGTH: 69
<212> TYPE: DNA
<213> ORGANISM: Artificial Sequence
<220> FEATURE:
<223> OTHER INFORMATION: Primer

<400> SEQUENCE: 19
ctcatcctcg gaccggagcc cactgatggc cagggaggct gaggtgccag acttggagcc    60
agagaatcg                                                           69

<210> SEQ ID NO 20
<211> LENGTH: 75
<212> TYPE: DNA
<213> ORGANISM: Artificial Sequence
<220> FEATURE:
<223> OTHER INFORMATION: Primer

<400> SEQUENCE: 20
caggcggagg tggatccggc ggtggcggat cgcagtctgt gctgactcag ccaccctcag    60
cgtctgggac ccccg                                                    75

<210> SEQ ID NO 21
```

-continued

<211> LENGTH: 43
<212> TYPE: DNA
<213> ORGANISM: Artificial Sequence
<220> FEATURE:
<223> OTHER INFORMATION: Primer

<400> SEQUENCE: 21
actcgcggcc caaccggcca tggccgaggt gcagctgttg gag         43

<210> SEQ ID NO 22
<211> LENGTH: 61
<212> TYPE: DNA
<213> ORGANISM: Artificial Sequence
<220> FEATURE:
<223> OTHER INFORMATION: Primer

<400> SEQUENCE: 22
caactttctt gtcgacttta tcatcatcat ctttataatc acctaggacc gtcagcttgg         60
t         61

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
acagtcataa tgaaatacct attgc         25

<210> SEQ ID NO 24
<211> LENGTH: 16
<212> TYPE: DNA
<213> ORGANISM: Artificial Sequence
<220> FEATURE:
<223> OTHER INFORMATION: Primer

<400> SEQUENCE: 24
gcacaggaga gtctca         16

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
caccatctcc agagacaatt cc         22

<210> SEQ ID NO 26
<211> LENGTH: 18
<212> TYPE: DNA
<213> ORGANISM: Artificial Sequence
<220> FEATURE:
<223> OTHER INFORMATION: Primer

<400> SEQUENCE: 26
ggccgtgtcc tcggctct         18

<210> SEQ ID NO 27
<211> LENGTH: 17
<212> TYPE: DNA
<213> ORGANISM: Artificial Sequence
<220> FEATURE:
<223> OTHER INFORMATION: Primer

```
<400> SEQUENCE: 27
tggtcaccgt gagcagc                                                    17

<210> SEQ ID NO 28
<211> LENGTH: 15
<212> TYPE: DNA
<213> ORGANISM: Artificial Sequence
<220> FEATURE:
<223> OTHER INFORMATION: Primer

<400> SEQUENCE: 28
ccgccggatc cacct                                                      15

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
caggcggagg tggatccggc                                                 20

<210> SEQ ID NO 30
<211> LENGTH: 17
<212> TYPE: DNA
<213> ORGANISM: Artificial Sequence
<220> FEATURE:
<223> OTHER INFORMATION: Primer

<400> SEQUENCE: 30
cgggggtccc agacgct                                                    17

<210> SEQ ID NO 31
<211> LENGTH: 19
<212> TYPE: DNA
<213> ORGANISM: Artificial Sequence
<220> FEATURE:
<223> OTHER INFORMATION: Primer

<400> SEQUENCE: 31
cgattctctg gctccaagt                                                  19

<210> SEQ ID NO 32
<211> LENGTH: 17
<212> TYPE: DNA
<213> ORGANISM: Artificial Sequence
<220> FEATURE:
<223> OTHER INFORMATION: Primer

<400> SEQUENCE: 32
ctcatcctcg gaccgga                                                    17

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
tcggcggagg aaccaagct                                                  19

<210> SEQ ID NO 34
```

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
tggccttgat attcacaaac gaat                                              24

<210> SEQ ID NO 35
<211> LENGTH: 38
<212> TYPE: DNA
<213> ORGANISM: Artificial Sequence
<220> FEATURE:
<223> OTHER INFORMATION: Primer

<400> SEQUENCE: 35
tccctgagac tctcctgtgc agcctctgga ttcacctt                               38

<210> SEQ ID NO 36
<211> LENGTH: 23
<212> TYPE: DNA
<213> ORGANISM: Artificial Sequence
<220> FEATURE:
<223> OTHER INFORMATION: Primer

<400> SEQUENCE: 36
ttccctggag cctggcggac cca                                               23

<210> SEQ ID NO 37
<211> LENGTH: 24
<212> TYPE: DNA
<213> ORGANISM: Artificial Sequence
<220> FEATURE:
<223> OTHER INFORMATION: Primer

<400> SEQUENCE: 37
ggaattgtct ctggagatgg tgaa                                              24

<210> SEQ ID NO 38
<211> LENGTH: 15
<212> TYPE: DNA
<213> ORGANISM: Artificial Sequence
<220> FEATURE:
<223> OTHER INFORMATION: Primer

<400> SEQUENCE: 38
gtccgccagg ctcca                                                        15

<210> SEQ ID NO 39
<211> LENGTH: 34
<212> TYPE: DNA
<213> ORGANISM: Artificial Sequence
<220> FEATURE:
<223> OTHER INFORMATION: Primer

<400> SEQUENCE: 39
cgctgctcac ggtgaccagt gtaccttggc ccca                                   34

<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40

-continued agagccgagg acacggccgt gtattactgt                                30

<210> SEQ ID NO 41
<211> LENGTH: 38
<212> TYPE: DNA
<213> ORGANISM: Artificial Sequence
<220> FEATURE:
<223> OTHER INFORMATION: Primer

<400> SEQUENCE: 41
agcgtctggg accccgggc agagggtcac catctctt                        38

<210> SEQ ID NO 42
<211> LENGTH: 28
<212> TYPE: DNA
<213> ORGANISM: Artificial Sequence
<220> FEATURE:
<223> OTHER INFORMATION: Primer

<400> SEQUENCE: 42
gggccgttcc tgggagctgc tgatacca                                  28

<210> SEQ ID NO 43
<211> LENGTH: 34
<212> TYPE: DNA
<213> ORGANISM: Artificial Sequence
<220> FEATURE:
<223> OTHER INFORMATION: Primer

<400> SEQUENCE: 43
gctcccagga acggccccca aactcctcat ctat                           34

<210> SEQ ID NO 44
<211> LENGTH: 32
<212> TYPE: DNA
<213> ORGANISM: Artificial Sequence
<220> FEATURE:
<223> OTHER INFORMATION: Primer

<400> SEQUENCE: 44
gacttggagc cagagaatcg gtcagggacc cc                             32

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
gtcagcttgg ttcctccgcc gaa                                       23

<210> SEQ ID NO 46
<211> LENGTH: 31
<212> TYPE: DNA
<213> ORGANISM: Artificial Sequence
<220> FEATURE:
<223> OTHER INFORMATION: Primer

<400> SEQUENCE: 46
ctccggtccg aggatgaggc tgattattac t                              31

<210> SEQ ID NO 47
<211> LENGTH: 60
<212> TYPE: DNA

```
<213> ORGANISM: Artificial Sequence
<220> FEATURE:
<223> OTHER INFORMATION: Primer

<400> SEQUENCE: 47
tacctattgc ctacggcagc cgctggattg ttattactcg cggcccagcc ggccatggcc        60

<210> SEQ ID NO 48
<211> LENGTH: 52
<212> TYPE: DNA
<213> ORGANISM: Artificial Sequence
<220> FEATURE:
<223> OTHER INFORMATION: Primer

<400> SEQUENCE: 48
ccgccggatc cacctccgcc tgaaccgcct ccaccgctgc tcacggtgac ca                52

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
tggccttgat attcacaaac gaat                                               24

<210> SEQ ID NO 50
<211> LENGTH: 18
<212> TYPE: DNA
<213> ORGANISM: Artificial Sequence
<220> FEATURE:
<223> OTHER INFORMATION: Primer

<400> SEQUENCE: 50
acggcagccg ctggattg                                                      18

<210> SEQ ID NO 51
<211> LENGTH: 130
<212> TYPE: PRT
<213> ORGANISM: Unknown
<220> FEATURE:
<223> OTHER INFORMATION: scFv-B11 Antibody Fragment

<400> SEQUENCE: 51
```

Leu Ala Ala Gln Pro Ala Met Ala Glu Val Gln Leu Leu Glu Ser Gly
 1               5                  10                  15

Gly Gly Leu Val Gln Pro Gly Gly Ser Leu Arg Leu Ser Cys Ala Ala
            20                  25                  30

Ser Gly Phe Thr Phe Ser Arg Tyr Ala Met Ser Trp Val Arg Gln Ala
        35                  40                  45

Pro Gly Lys Gly Leu Glu Trp Val Ser Ala Ile Ser Gly Ser Gly Gly
    50                  55                  60

Gly Thr His Tyr Ala Asp Ser Val Lys Gly Arg Phe Thr Ile Ser Arg
65                  70                  75                  80

Asp Asn Ser Lys Asn Thr Leu Tyr Leu Gln Met Asn Ser Leu Arg Ala
                85                  90                  95

Glu Asp Thr Ala Val Tyr Tyr Cys Ala Arg Ile Gly Gln Phe Trp Gly
            100                 105                 110

Gln Gly Thr Leu Val Thr Val Ser Ser Gly Gly Gly Ser Gly Gly Gly
        115                 120                 125

Ser Gln

-continued

```
                130

<210> SEQ ID NO 52
<211> LENGTH: 130
<212> TYPE: PRT
<213> ORGANISM: Unknown
<220> FEATURE:
<223> OTHER INFORMATION: scFv-B11 Antibody Fragment

<400> SEQUENCE: 52

Leu Ala Ala Gln Pro Ala Met Ala Glu Val Gln Leu Leu Glu Ser Gly
  1               5                  10                  15

Gly Gly Leu Val Gln Pro Gly Gly Ser Leu Arg Leu Ser Cys Ala Ala
             20                  25                  30

Ser Gly Phe Thr Phe Ser Gly Tyr Ala Met Ser Trp Val Arg Gln Ala
         35                  40                  45

Pro Gly Lys Gly Leu Glu Trp Val Ser Ala Ile Ser Gly Ser Gly Gly
     50                  55                  60

Ser Thr His Tyr Ala Asp Ser Val Lys Gly Arg Phe Thr Ile Ser Arg
 65                  70                  75                  80

Asp Asn Ser Lys Asn Thr Leu Tyr Leu Gln Met Asn Ser Leu Arg Ala
                 85                  90                  95

Glu Asp Thr Ala Val Tyr Tyr Cys Ala Arg Ile Gly Arg Phe Trp Gly
            100                 105                 110

Gln Gly Thr Leu Val Thr Val Ser Ser Gly Gly Gly Ser Gly Gly Gly
        115                 120                 125

Ser Gln
    130

<210> SEQ ID NO 53
<211> LENGTH: 130
<212> TYPE: PRT
<213> ORGANISM: Unknown
<220> FEATURE:
<223> OTHER INFORMATION: scFv-B11 Antibody Fragment

<400> SEQUENCE: 53

Leu Ala Ala Gln Pro Ala Met Ala Glu Val Gln Leu Leu Glu Ser Gly
  1               5                  10                  15

Gly Gly Leu Val Gln Pro Gly Gly Ser Leu Arg Leu Ser Cys Ala Ala
             20                  25                  30

Ser Gly Phe Thr Phe Ser Ser Tyr Ala Met Ser Trp Val Arg Gln Ala
         35                  40                  45

Pro Gly Lys Gly Leu Glu Trp Val Ser Ala Ile Ser Gly Ser Gly Gly
     50                  55                  60

Ser Thr His Tyr Ala Asp Ser Val Lys Gly Arg Phe Thr Ile Ser Arg
 65                  70                  75                  80

Asp Asn Ser Lys Asn Thr Leu Tyr Leu Gln Met Asn Ser Leu Arg Ala
                 85                  90                  95

Glu Asp Thr Ala Val Tyr Tyr Cys Ala Arg Ile Gly Gln Phe Trp Gly
            100                 105                 110

Gln Gly Thr Leu Val Thr Val Ser Ser Gly Gly Gly Ser Gly Gly Gly
        115                 120                 125

Ser Gln
    130

<210> SEQ ID NO 54
<211> LENGTH: 130
```

-continued

```
<212> TYPE: PRT
<213> ORGANISM: Unknown
<220> FEATURE:
<223> OTHER INFORMATION: scFv-B11 Antibody Fragment

<400> SEQUENCE: 54

Leu Ala Ala Gln Pro Ala Met Ala Glu Val Gln Leu Leu Glu Ser Gly
 1               5                  10                  15

Gly Gly Leu Val Gln Pro Gly Gly Ser Leu Arg Leu Ser Cys Ala Ala
                20                  25                  30

Ser Gly Phe Thr Phe Ser Ser Tyr Ala Met Ser Trp Val Arg Gln Ala
            35                  40                  45

Pro Gly Lys Gly Leu Glu Trp Val Ser Ala Ile Ser Gly Ser Gly Gly
        50                  55                  60

Ser Thr Tyr Tyr Ala Asp Ser Val Lys Gly Arg Phe Thr Ile Ser Arg
65                  70                  75                  80

Asp Asn Ser Lys Asn Thr Leu Tyr Leu Gln Met Asn Ser Leu Arg Ala
                85                  90                  95

Glu Asp Thr Ala Val Tyr Tyr Cys Ala Arg Ile Gly Gln Phe Trp Gly
            100                 105                 110

Gln Gly Thr Leu Val Thr Val Ser Ser Gly Gly Gly Ser Gly Gly Gly
        115                 120                 125

Ser Gln
130
```

METHOD FOR IN VITRO MOLECULAR EVOLUTION OF PROTEIN FUNCTION

This application is a continuation application of U.S. patent application Ser. No. 10/118,100 filed Apr. 8, 2002, now U.S. Pat. No. 6,989,250 B2, which is a continuation of U.S. patent application Ser. No. 09/341,711 filed Sep. 21, 1999, now abandoned, which is a §371 filing of PCT/GB98/00219 filed Jan. 26, 1998, which claims priority to GB9701425.2 filed Jan. 24, 1997. The foregoing applications are incorporated by reference herein.

FIELD OF THE INVENTION

The present invention relates to a method for in vitro molecular evolution of protein function. Particularly, but not exclusively, it relates to the shuffling of polynucleotide sequence segments within a coding sequence.

BACKGROUND OF THE INVENTION

Protein function can be modified and improved in vitro by a variety of methods, including site directed mutagenesis (Moore et al, 1987) combinatorial cloning (Huse et al, 1989; Marks et al, 1992) and random mutagenesis combined with appropriate selection systems (Barbas et al, 1992).

The method of random mutagenesis together with selection has been used in a number of cases to improve protein function and two different strategies exist. Firstly, randomisation of the entire gene sequence in combination with the selection of a variant (mutant) protein with the desired characteristics, followed by a new round of random mutagenesis and selection. This method can then be repeated until a protein variant is found which is considered optimal (Moore et al, 1996). Here, the traditional route to introduce mutations is by error prone PCR (Leung et al, 1989) with a mutation rate of ≈0.7%.

Secondly, defined regions of the gene can be mutagenized with degenerate primers, which allows for mutation rates up to 100% (Griffiths et al, 1994; Yang et al, 1995). The higher the mutation rate used, the more limited the region of the gene that can be subjected to mutations.

Random mutation has been used extensively in the field of antibody engineering. In vivo formed antibody genes can be cloned in vitro (Larrick et al, 1989) and random combinations of the genes encoding the variable heavy and light genes can be subjected to selection (Marks et al, 1992). Functional antibody fragments selected can be further improved using random mutagenesis and additional rounds of selections (Hoogenboom et al, 1992).

The strategy of random mutagenesis is followed by selection. Variants with interesting characteristics can be selected and the mutagenized DNA regions from different variants, each with interesting characteristics, are combined into one coding sequence (Yang et al, 1995). This is a multi-step sequential process, and potential synergistic effects of different mutations in different regions can be lost, since they are not subjected to selection in combination. Thus, these two strategies do not include simultaneous mutagenesis of defined regions and selection of a combination of these regions. Another process involves combinatorial pairing of genes which can be used to improve e.g. antibody affinity (Marks et al, 1992). Here, the three CDR-regions in each variable gene are fixed and this technology does not allow for shuffling of individual CDR regions between clones.

Selection of functional proteins from molecular libraries has been revolutionized by the development of the phage display technology (Parmley et al, 1987; McCafferty et al, 1990; Barbas et al, 1991). Here, the phenotype (protein) is directly linked to its corresponding genotype (DNA) and this allows for directly cloning of the genetic material which can then be subjected to further modifications in order to improve protein function. Phage display has been used to clone functional binders from a variety of molecular libraries with up to $10^{11}$ transformants in size (Griffiths et al, 1994). Thus, phage display can be used to directly clone functional binders from molecular libraries, and can also be used to improve further the clones originally selected.

Random combination of DNA from different mutated clones is a more efficient way to search through sequence space. The concept of DNA shuffling (Stemmer, 1994) utilises random fragmentation of DNA and assembly of fragments into a functional coding sequence. In this process it is possible to introduce chemically synthesised DNA sequences and in this way target variation to defined places in the gene which DNA sequence is known (Crameri et al, 1995). In theory, it is also possible to shuffle DNA between any clones. However, if the resulting shuffled gene is to be functional with respect to expression and activity, the clones to be shuffled have to be related or even identical with the exception of a low level of random mutations. DNA shuffling between genetically different clones will generally produce non-functional genes.

SUMMARY OF THE INVENTION

At its most general the present invention provides a method of obtaining a polynucleotide sequence encoding a protein of desired characteristics comprising the steps of incorporating at least one variant nucleotide region (variant motif) into defined nucleotide regions (scaffold sequence) derived from a parent polynucleotide sequence. The new assembled polynucleotide sequence may then be expressed and the resulting protein screened to determine its characteristics.

The present method allows protein characteristics to be altered by modifying the polynucleotide sequence encoding the protein in a specific manner. This may be achieved by either a) replacing a specified region of the nucleotide sequence with a different nucleotide sequence or b) by mutating the specified region so as to alter the nucleotide sequence. These specified regions (variant motifs) are incorporated within scaffold or framework regions (scaffold sequence) of the original polynucleotide sequence (parent polynucleotide sequence) which when reassembled will encoded a protein of altered characteristics. The characteristics of the encoded protein are altered as a result of the amino acid sequence being changed corresponding to the changes in the coding polynucleotide sequence.

Rather than modifying a sequence at random and then relying on extensive screening for the desired coded protein, the present inventors have found it desirable to provide a method which modifies selected segments (variant motifs) of a protein while maintaining others.

The variant motifs may be segments of nucleotide sequence that encode specified regions of a protein. For example, functional regions of a protein (e.g. loops) or CDR regions in an antibody.

The scaffold sequence may be segments of nucleotide sequence which it is desirable to maintain, for example they may encode more structural regions of the protein, e.g. framework regions in an antibody.

The variant motifs may be nucleotide segments which originated from the same polynucleotide sequence as the scaffold sequence, i.e. the parent polynucleotide sequence, but which have been mutated so as to alter the coding sequence from that in the parent. For example, the parent polynucleotide sequence may encode an antibody. The nucleotide sequences encoding the CDR regions of the antibody (variant motifs) may be selected from the remaining coding sequence of the parent polynucleotide, mutated and then reassembled with scaffold sequence derived from the remaining coding sequence. The expressed antibody will differ from the wild type antibody expressed by the parent polynucleotide in the CDR regions only.

Alternatively, the variant motif may be derived from a polynucleotide sequence encoding a protein sequentially related to the protein encoded by the parent polynucleotide sequence. For example, the CDR regions from one antibody (antibody A) may be replaced by the CDR regions of another antibody (antibody B).

In each case the resulting expressed protein can be screened for desired characteristics. Desirable characteristics may be changes in the biological properties of the protein. For example, the tertiary structure of the protein may be altered. This may affect its binding properties, the ability for it to be secreted from cells or into cells or, for enzymes, its catalytic properties. If the protein is an antibody or part thereof it may be desirable to alter its ability to specifically bind to an antigen or to improve its binding properties in comparison to the parent antibody.

According to one aspect of the present invention, there is provided a method of obtaining a protein of desired characteristics by incorporating variant peptide regions (variant motifs) into defined peptide regions (scaffold sequence), which method comprises the steps of:

(a) subjecting parent polynucleotide sequence encoding one or more protein motifs to mutagenesis to create a plurality of differently mutated derivatives thereof, or obtaining parent polynucleotide encoding a plurality of variant protein motifs of unknown sequence, (b) providing a plurality of pairs of oligonucleotides, each pair representing spaced-apart locations on the parent polynucleotide sequence bounding an intervening variant protein motif, and using each said pair of oligonucleotides as amplification primers to amplify the intervening motif;

(c) obtaining single-stranded nucleotide sequence from the thus-isolated amplified nucleotide sequence; and (d) assembling nucleotide sequence encoding a protein by incorporating nucleotide sequences derived from step (c) above with nucleotide sequence encoding scaffold sequence.

The method may further comprise the step of expressing the resulting protein encoded by the assembled nucleotide sequence and screening for desired properties.

Preferably the parent polynucleotide sequence is DNA from which is derived DNA sequences encoding the variant motifs and scaffold sequences.

Preferably the pairs of oligonucleotides are single-stranded oligonucleotide primers. One of said pair may be linked to a member of a specific binding pair (MSBP). The MSBP is preferably biotin, whose specific binding partner could for example be streptavidin. By using the specific binding pair the amplified nucleotide sequences may be isolated.

Random mutation can be accomplished by any conventional method; but a suitable method is error-prone PCR.

The protein in question could, for example, be an antibody or antibody fragment having desirable characteristics. Example of antibody fragments, capable of binding an antigen or other binding partner, are the Fab fragment consisting of the VL, VH, Cl and CH1 domains; the Fd fragment consisting of the VH, and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

In one approach, after randomly mutating DNA encoding the antibody, or a portion of that DNA (e.g. that which encodes the Fab regions or variable regions), oligonucleotide primers could be synthesised corresponding to sequences bounding the CDRs (the variant motifs), so that DNA encoding the CDRs are amplified, along with any mutations that may have occurred in the CDRs. These can be incorporated in the reassembly of the antibody coding sequence, using the amplified CDR DNA sequences and the unmutated scaffold framework (FR) DNA sequences, resulting in the expression of an antibody which has a novel combination of CDRs, and potentially having altered properties which can be selected or screened for in conventional manner.

In another approach, rather than mutate CDRs and reassembling them back into an antibody which will be closely related to the parent antibody from which the CDRs were derived, the CDRs may be taken from one or more existing antibodies, but be of unknown sequence. Using oligonucleotide primers representing sequences bounding the various CDRs, the individual CDRs can be amplified, isolated and assembled into a predetermined scaffold.

Of course, combinations of the foregoing approaches could be used, with CDRs taken from one or more parent antibodies, and assembled into a scaffold to produce a completely new, secondary antibody, then, after screening to obtain a secondary antibody with desired characteristics, the DNA encoding it could be mutated, the CDRs amplified and isolated, and then reassembled with unmutated non-CDR (scaffold) DNA from the secondary antibody, to produce variants of the secondary antibody which are mutated in the CDRs, and which can be screened for improved properties with respect to the originally selected secondary antibody.

The present invention allows a novel way for the isolation of DNA sequences from genetically related clones that are functionally different. Genetically related clones are those that belong to a particular structural class, for example immunoglobulins or alpha-beta-barrels. The invention allows for both isolation and random combination into a given DNA sequence of functional sequences from these related clones. These functional sequences may be loops that perform binding or catalysis.

The concept of the invention is demonstrated using antibody molecules where CDR-regions from different germline sequences can be isolated and randomly combined into a defined framework sequence. The invention expands the complexity of the molecular libraries that can be selected using phage display. The concept of the invention is also demonstrated by the affinity maturation of antibody fragments by the isolation and random combination of mutated CDR-regions.

It is not possible to use the DNA shuffling concept (Stemmer, 1994) to isolate specific sequences and randomly combine these into a given gene sequence, as it is not possible to amplify individual DNA regions formed in vivo using DNA shuffling. Combination of entire gene sequences is possible, but here defined regions cannot be shuffled. Rather all the DNA is shuffled. Thus, DNA sequences from genetically related clones that are functionally different, e.g. proteins that belong to structural classes like immunoglobulins or alphabeta-barrels, cannot be shuffled in such a way that specific regions are kept constant and other regions are shuffled.

The system provided by the present invention offers a simple way to randomly combine functional regions of proteins (e.g. loops) to a defined (specifically selected) scaffold, i.e. shuffling of loops to a given protein tertiary structure in order to find new protein functions. Furthermore, the DNA shuffling technology introduces mutations at a rate of 0.7% (Stemmer, 1994). Thus, the known DNA shuffling technology (Stemmer, 1994) does not allow for shuffling of unmutated regions, since the process itself introduces mutations at random positions, including the scaffold regions.

In contrast, the invention allows for mutagenesis of defined DNA-sequences together with shuffling and assembly of these pieces of DNA into a coding region, and will allow for mutagenesis of defined regions and subsequent selection of these regions in combination.

The invention allows for different regions of DNA from different sequences (clones) to be shuffled and randomly combined. This increases the genetic variation from which functional antibody fragments are selected and will thus increase the probability of selecting proteins with the desired characteristics. It can be realised that by randomly shuffling as few as a hundred CDRs at each position in the VH and VL of an fragment, as many as $10^{12}$ combinations may be obtained thereby extending the variability normally found in the immune system.

The invention provides amplification of defined regions from e.g. a cDNA library using two primers of which one is biotinylated. Using the MSBP, e.g. biotin, group, single stranded DNA can be isolated and used in the gene assembly process. The present inventors have demonstrated this with the amplification of diverse CDR regions from an antibody gene library and the combination of these CDR regions randomly to a given framework region. Thus, defined regions of DNA (framework regions) can be interspaced by random regions of DNA (CDR regions), which have an in vivo origin or can be chemically synthesized.

The present invention also provides polynucleotide sequences and the proteins they encoded produced by the method described above. There is also provided vectors incorporating the polynucleotide sequences and host cell transformed by the vectors.

The present invention also provides a polynucleotide library comprising polynucleotides created by the method described above which may be used for phage display.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

FIG. 4A: Assembly of genes for the VH-domain. The template is scFv-B11 mutated with error prone PCR. An individual CDR is amplified using two primers adjacent to the particular CDR and one of these primers is biotinylated at the 5' end. The individual CDR is amplified and double-stranded DNA (dsDNA) is produced with the mutations focused to the CDR since the two amplification primers do not contain any mutations. This DNA is separated into two single stranded DNA molecules. The molecule without biotin is used in gene assembly. Primers 725, 729, 730, 728, 727 are synthesized in a DNA synthesizer and primers H2, H3, H5 contain mutated CDR and are amplified as above. FIG. 4B: Assembly of genes for the VL-domain. CDRs are amplified in the same way as in A. Primers 759, 738, 745, 744, 880 are synthesized in a DNA synthesizer and primers L2, L3, L5 contain mutated CDR and are amplified as above.

FIG. 7 shows the length of CDR3 heavy chain from different clones. These CDR regions have been amplified from different germline sequences and randomly cloned to a defined framework region (from DP-47 sequence).

FIG. 8 shows a schematic representation of amplification of defined sequences of DNA and the shuffling of these into a master framework. All the oligonucleotides used in the gene assembly are amplified by PCR, but only the CDR regions contain any genetic variation. FIG. 8B: Assembly of genes for the VL-domain. In principle the same procedure as in A. Primers L1, L4, L6 are amplified and produced by PCR and contain no variation. LCDR1, LCDR2, LCDR3 contain different CDR. Primers BT7 and BT12 are synthesized in a DNA-synthesizing machine.

Figure 9A:
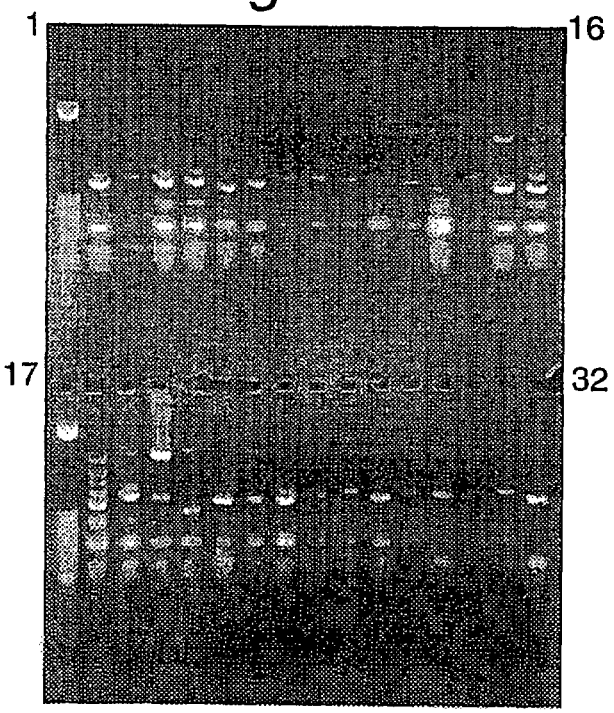
FIG. 9A shows the variation in a library constructed according to FIG. 8. The scFv region of library clones and original scFv-B11, binding to FITC (fluorescein-iso-thiocyanate) was synthesized by PCR. Purified PCR products were cut with BstNI and separated on a 2.5% agarose gel. Clones 1-15 are in lane 2-16, clones 16-29 are in lane 18-31. Original scFv-B11 is in lane 32. Analysis revealed that 28 clones could be sorted in 13 different groups according to restriction pattern and fragment size. Eight clones (1, 2, 8, 10, 12, 16, 26, 27) were unique, 2 clones (17, 24) appeared similar, 1 group of clones (18, 23, 29) had 3 similar members, 2 groups (5, 15, 14, 19) and (3, 4, 6, 11) had 4 members and 1 group (7, 9, 13, 20, 21, 22, 25) had 7 similar members. This experiment underestimates the variation in the library since BstNI detects only a fraction of sequence variability. In addition, the gel resolution did not allow the detection of minor size differences and did not resolve fragments below 100 bp.
Figure 9B:
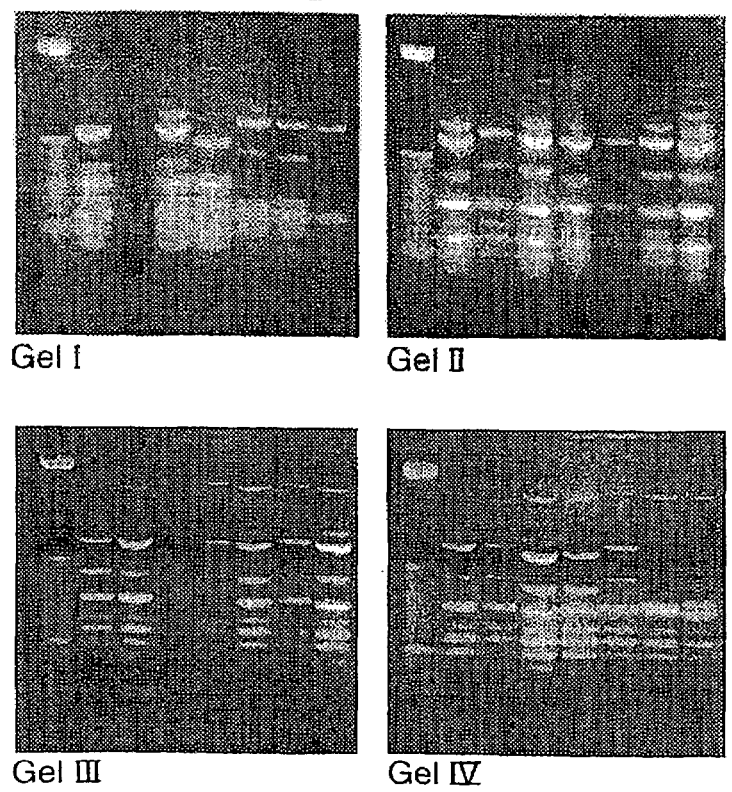
FIG. 9B shows clones showing similar restriction pattern in the experiment exemplified in FIG. 9A cut by both BstNI and BamHI and separated on 3% agarose gels. To facilitate comparison, the groups of similar clones described in experiment A were put together on the gels. Clone 8 and 28 from experiment A were excluded due to space limitations.

Gel I) Lane 1-8; standard, clone 5, 15, 14, 19, 2, 27, original scFv-B11, respectively Gel II) Lane 1-8; standard, clone 16, 17, 24, 18, 23, 29, 26, respectively Gel III) Lane 1-8; standard, clone 7, 9, 13, 20, 21, 22, 25, respectively Gel VI) Lane 1-8; standard, clone 3, 4, 6, 11, 1, 10, 12, respectively Under these improved experimental conditions, essentially all clones had different restriction patterns/fragments sizes. All clones were different from the original scFv-B11 gene (lane 8, gel 1). Moreover, the groups of clones which appeared similar in FIG. 9A were found to be different as analyzed in FIG. 9B. See clone 5, 15, 14, 19 (lanes 2-5 gel I), clone 17, 24 (lanes 3-4 gel II), clone 18, 23, 29 (lanes 5-7 gel II), clones 7, 9, 13, 20, 21, 22, 25, (lanes 2-8, gel III) and clones 3, 4, 6, 11 (lanes 2-5 gel IV).

In conclusion, these experiments suggest that the library contains high variability.

DETAILED DESCRIPTION AND EXEMPLIFICATION OF THE INVENTION

Figure 1:
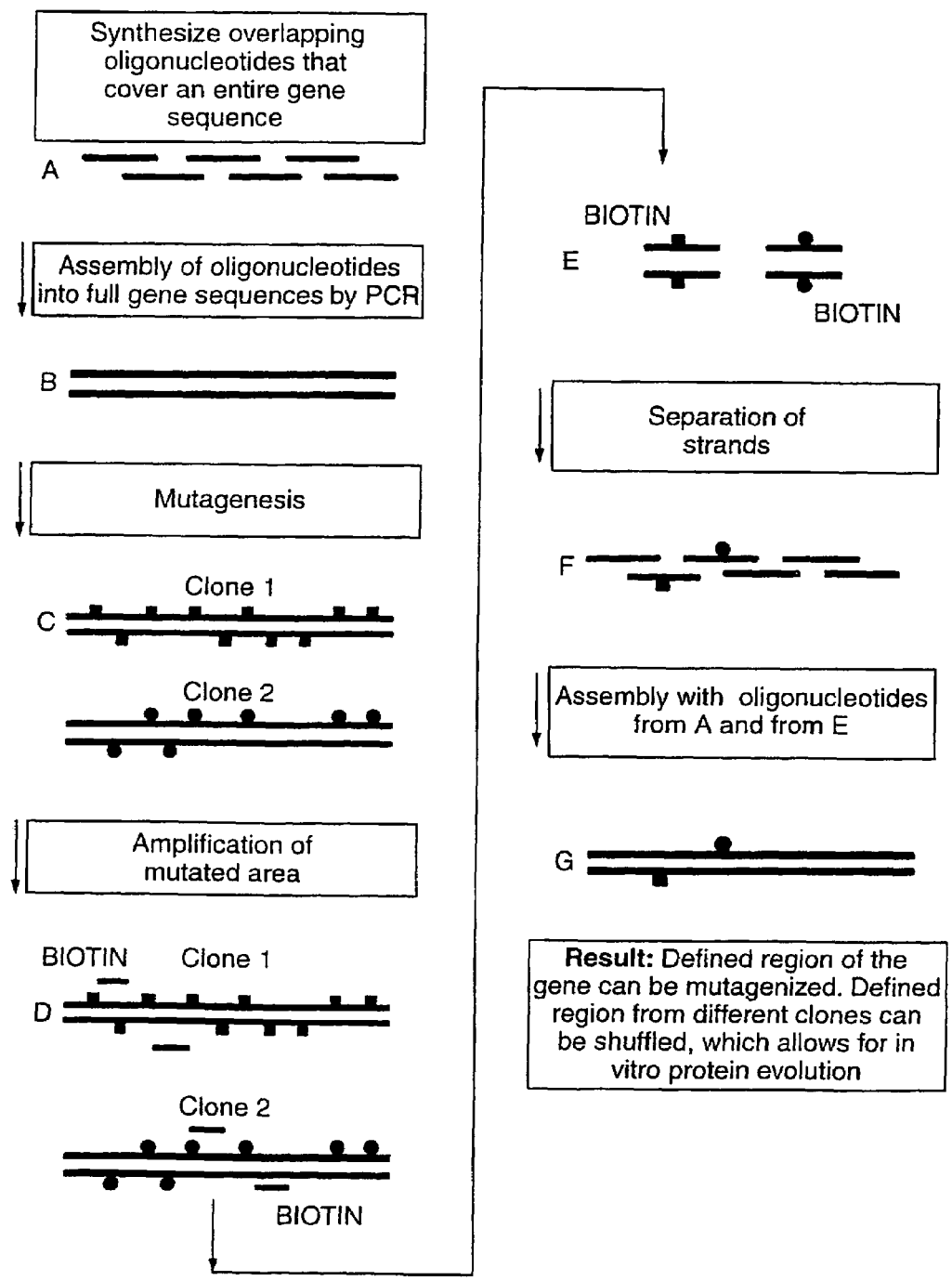
FIGS. 1A to 1G show shuffling of specific DNA sequences between different clones, based on the assembly of gene sequences from a set of overlapping oligo-nucleotides following a one-step PCR protocol.

One aspect of the DNA shuffling procedure can be illustrated by the following steps in FIG. 1.

A: A gene coding for a protein of interest is divided into overlapping oligonucleotides.

B: The oligonucleotides are assembled using PCR into a full length gene-sequence.

C: The gene sequence is subjected to mutagenesis, e.g. by error-prone PCR.

D: Pairs of oligonucleotides are synthesized, each pair covering a region defined by one of the oligonucleotides in step A above, except for a region located in the middle of the step A oligonucleotide. This uncovered region is the DNA sequence that can be shuffled after PCR amplification. These two synthesised oligonucleotides can thus be used as amplification primers to amplify the uncovered region.

E: One of these amplification primers is biotinylated and the double-stranded PCR product can then be isolated using well-known strepavidin systems.

F: From the thus isolated amplified oligonucleotides can be obtained a single-stranded DNA sequence containing DNA from the uncovered region mentioned above, which can then be used as oligo-nucleotide in a new assembly of the gene sequence as described in step A.

G: If DNA sequences from different clones and from different regions of the mutated gene sequence are amplified and made single-stranded, they will combine randomly in the PCR process of gene assembly. This random combination is the basis for in vitro molecular evolution.

EXAMPLES

The present inventors have demonstrated the concept of shuffling of defined DNA in different experimental settings. Firstly, the shuffling of in vitro mutated CDR regions in an antibody fragment for affinity maturation purposes (example 1 and 2) is exemplified and secondly the shuffling of in vivo formed CDRs for creation of a highly variable antibody library (example 3 and 4) is exemplified.

1. Affinity Maturation

Figure 4:
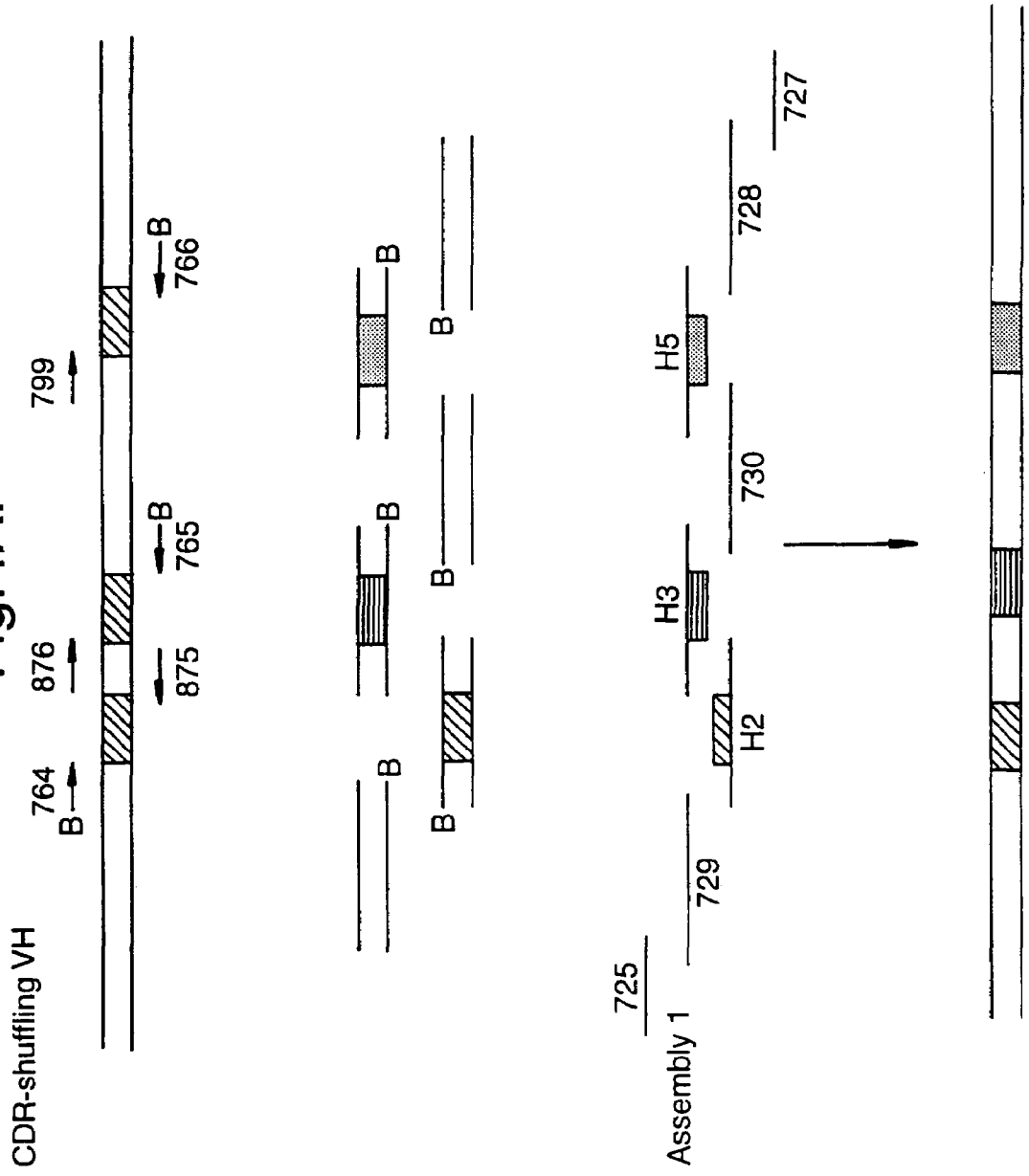
FIG. 4 shows a schematic representation of amplification of defined sequences of DNA and the shuffling of these into a master framework. Only the CDR regions are amplified.

A model system was developed, based on the scFv-B11 antibody fragment which binds to FITC. The full-length gene encoding this scFv was assembled from a set of 12 oligonucleotides (FIG. 4A and FIG. 4B) representing the known DNA sequence of the scFv-B11, and the functional binding of the gene product to FITC could be verified. This gene sequence was then mutagenised using error-prone PCR, and the DNA encoding the CDR regions were amplified as described above, using the amplification primers, one of which is biotinylated. (The CDR regions are the parts of the antibody molecule involved in binding the antigen, in this case FITC).

Figure 2:
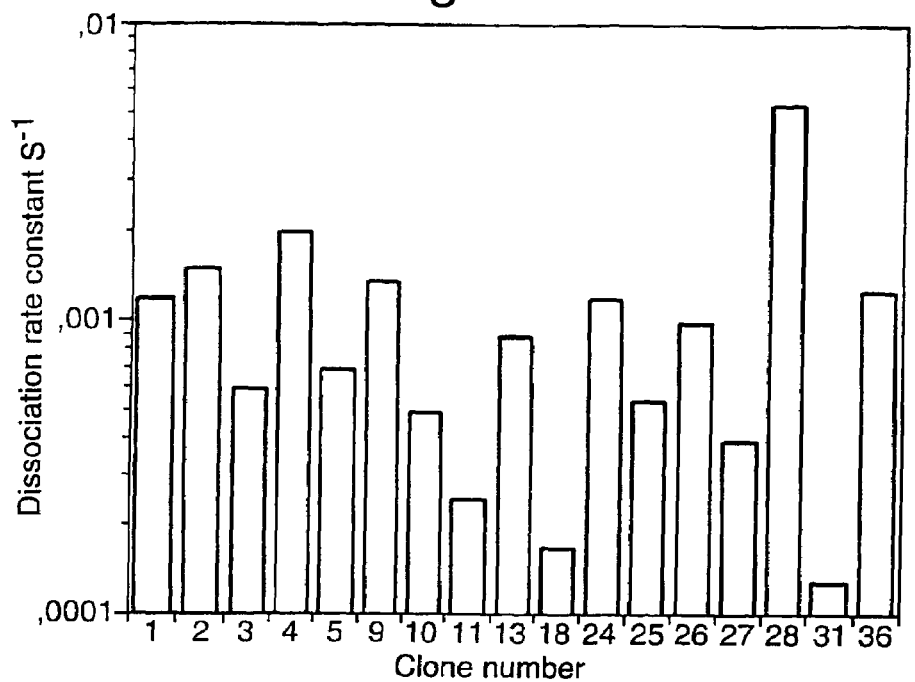
FIG. 2 shows different dissociation rate constants for different CDR-shuffled clones. A low bar represents slow dissociation-rate, a high bar represents a fast dissociation-rate. Clone 36 is the original non-mutated antibody fragment.

All six CDR regions were amplified and a new gene was assembled using six oligonucleotides selected from the first assembly of 12 oligonucleotide (see above) (these were not mutagenized) and six from the amplification of mutagenized CDR regions. Selection of functional antibody fragments that bound FITC was carried out using phage display. 50% of the clones bound FITC with different dissociation-rates than did the original scFv-B11, as measured in the BIAcore biosensor (FIG. 2). This demonstrates that the clones were changed in the way they recognized FITC.

Figure 3:
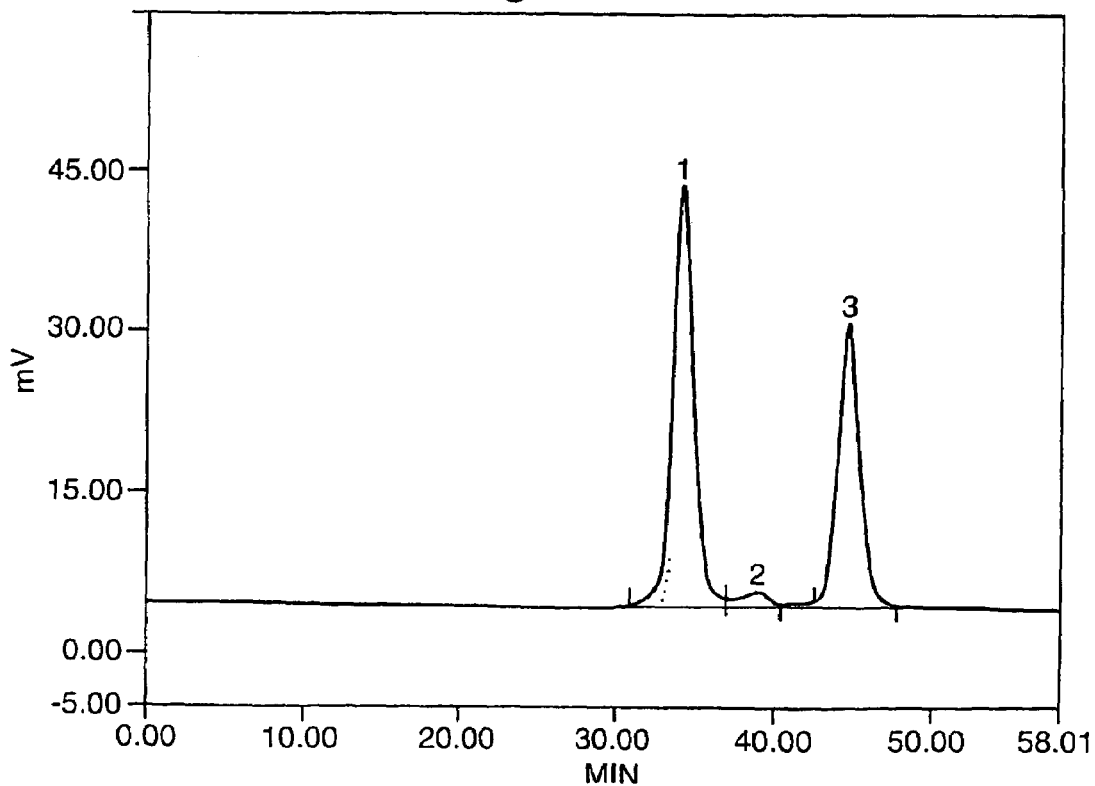
FIG. 3 shows the results of affinity purified scFv antibody fragment assayed on HPLC, Superose S-200 FPLC-column (Pharmacia) in PBS buffer. Peak 1 is the monomeric form of the antibody fragment, peak 2 is a small amount of impurity and peak 3 is NaN3 (sodium azid), used as a preservative.

Of the 16 clones identified to bind FITC in BIAcore (FIG. 2) clones 3, 11, 27 and 31 were chosen to be analyzed in more detail as these clones exhibited the larger changes in off-rates. These clones were expressed and affinity-purified on a column conjugated with FITC-BSA and eluted with a low pH buffer. The purified scFv-antibody fragments were further purified and analyzed with HPLC, using a Pharmacia Superdex 200 FPLC column with the capacity to separate the monomeric and dimeric form of the antibodies. In all clones the monomeric form dominated (typical size profile is shown in FIG. 3). This was then purified and used in detailed analysis of affinity using a BIAcore biosensor (Table 1).

TABLE 1

| Affinity determination of selected. | | | |
|---|---|---|---|
| Clone | $k_{ASS} (M^{-1} S^{-1})$ | $k_{DISS} (S^{-1})$ | $K_A (M^{-1})$ |
| #3 | $2.0 \times 10^5$ | $4.3 \times 10^{-3}$ | $4.8 \times 10^7$ |
| #11 | $2.6 \times 10^5$ | $3.3 \times 10^{-3}$ | $7.8 \times 10^7$ |
| #27 | $5.0 \times 10^5$ | $16.0 \times 10^{-3}$ | $3.1 \times 10^7$ |
| #31 | $1.2 \times 10^5$ | $5.4 \times 10^{-3}$ | $2.1 \times 10^7$ |
| (FITC-B11 original) | $2.7 \times 10^5$ | $9.7 \times 10^{-3}$ | $2.8 \times 10^7$ |

Clone #11 exhibited an affinity 2.8 times higher than the original scFv-B11 antibody fragment. This increase is based on a slower off-rate. One clone (#27) showed 2 times increase in association-rate. However, the overall affinity of this clone was similar to the original FITC-B11 clone due to a faster dissociation-rate. The distribution of different association and dissociation-rates among the clones was considered a source for CDR-reshuffling for further improvement of affinities.

Figure 5:
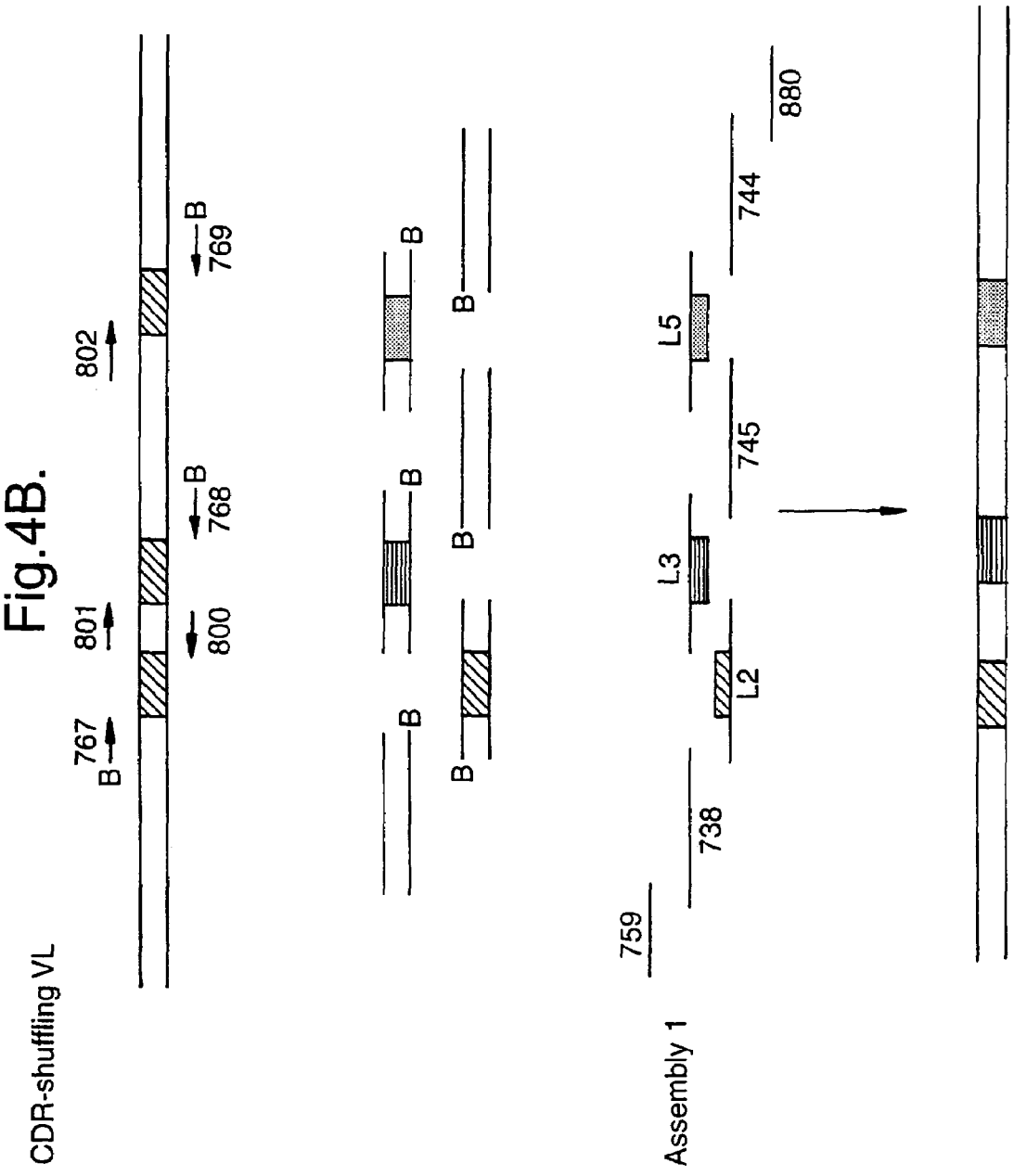
FIG. 5 shows the alignment of the peptide sequences for clones 3, 11 and 31 with the original non-mutated antibody fragment (wt). wherein the peptide sequences for clones 3, 11 and 31, and the orignal non-mutated antibody fragment (wt) are SEQ ID NOS. 51 to 54 respectively. The CDR-regions are marked. Mutations in clones 3, 11 and 31 are underlined.

Three clones were sequenced. In the VH region (i.e. half of the scFv-B11 and carrying three CDR regions) the mutations found were all in the CDR regions as expected, since these were the only regions mutagenized and amplified using the amplification primers. Interestingly, all the CDR regions were different and carried different mutations (FIG. 5). However, in the case of CDR region 2, the same mutation was found (a tyrosine to histidine substitution) in all 3 clones (the rest of CDR regions differed between the clones).

Furthermore, the mutation rates were found to be in between 2% and 4%, as determined from the base changes in the 90 bp long sequence built up from three CDR regions is together. This is more than the error-prone PCR mutation rate, and indicates that there is combination of individual CDR regions from different clones.

2. Affinity Maturation-Reshuffling

In order to perform a second shuffling (reshuffling), clones selected for their binding affinity to FITC were used in an additional round of CDR-amplification and library construction. In theory, the reshuffled library will contain mutated shuffled CDR-regions, selected for improved binding to FITC. In this way, new combinations of CDR-regions, improved with respect to binding, could be constructed and the library subjected to selection for binders with improved affinities.

The pool of all clones obtained from the selection procedure (as detailed in example 1) were used as template for CDR amplifications. One amplification was carried out for each CDR using primers listed in Table 2.

TABLE 2

Sequences for primers used in CDR-shuffling.
B = Biotin labeled 5' primer

CDR Reamplification Primers
 764 5' B-GTC CCT GAG ACT CTC CTG TGC AGC CTC TGG ATT CAC CTT T 3'

875 5' TCC CTG GAG CCT GGC GGA CCC A 3'

876 5' CGC CAG GCT CCA GGG AAG GGG CTG GAG TGG GTC TCA 3'

765 5' B-GGA ATT GTC TCT GGA GAT GGT GAA 3'

799 5' GAG CCG AGG ACA CGG CCG TGT ATT ACT GTG CAA GA 3'

766 5' B-GCG CTG CTC ACG GTG ACC AGG GTA CCT GGG CCC CA 3'

767 5' B-AGC GTC TGG GAC CCC CGG GCA GAG GGT CAC CAT CTC TTG T 3'

800 5' GGG CCG TTC CTG GGA GCT GCT GGT ACC A 3'

801 5' GCT CCC AGG AAC GGC CCC CAA ACT CCT CAT CTA T 3'

768 5' B-GAC TTG GAG CCA GAG AAT CGG TCA GGG ACC CC 3'

802 5' CTC CGG TCC GAG CAT GAG GCT GAT TAT TAC TGT 3'

769 5' B-CGT CAG CTT GGT TCC TCC GCC GAA 3'

Framework VH
 727 5' CCG CCG GAT CCA CCT CCG CCT GAA CCG CCT CCA CCG CTG CTC
       ACG GTG ACC A 3'

728 5' GAC CGA TGG ACC TTT GGT ACC GGC GCT GCT CAC GGT GAC CA 3'

729 5' GAG GTG CAG CTG TTG GAG TCT GGG GGA GGC TTG GTA CAG CCT
       GGG GGG TCC CTG AGA CTC TCC TGT 3'

730 5' GGC CGT GTC CTC GGC TCT CAG GCT GTT CAT TTG CAG ATA CAG
       CGT GTT CTT GGA ATT GTC TCT GGA GAT GGT 3'

Framework VL
 738 5' CAG TCT GTG CTG ACT CAG CCA CCC TCA GCG TCT GGG ACC CCC
       G 3'

744 5' ACT AGT TGG ACT AGC CAC AGT CCG TGG TTG ACC TAG GAC CGT
       CAG CTT GGT TCC TCC GC 3'

745 5' CTC ATC CTC GGA CCG GAG CCC ACT CAT GGC CAG GGA GGC TGA
       GGT GCC ACA CTT GGA GCC ACA GAA TCG 3'

1129 5' CAG GCG GAG GTG GAT CCG GCG GTG GCG GAT CGC AGT CTG TGC
       TGA CTC AGC CAC CCT CAG CGT CTG GGA CCC CG 3'

TABLE 2-continued

Sequences for primers used in CDR-shuffling.
B = Biotin labeled 5' primer

Amplification primers VH/VL Assembly
1125 5' ACT CGC GGC CCA ACC GGC CAT GGC CGA GGT GCA GCT GTT GGA
     G 3'

1126 5' CAA CTT TCT TGT CGA CTT TAT CAT CAT CAT CTT TAT AAT CAC
     CTA GGA CCG TCA GCT TGG T 3'

The amplification was peformed according to following parameters: 100 ng template ($1.6 \times 10^8$ CFU bacteria grown for 6 h), 60 pmol each primer, 5 Units PFU polymerase (Stratagene), 1×PFU buffer, 500 µM dNTPs, reaction volume 100 µl, preheat 96° C. for 10 minutes, 96° C. for 1 minute: 68° C. for 1 minute: 72° C. for 1 minute for 25 cycles, 72° C. for 10 minutes. This procedure was essentially the same as for CDR amplification in Example 1. The amplified CDR were used for assembly into VH and VL encoding sequence according to FIG. 1, 4A, 4B and Table 3.

TABLE 3

PCR parameters for the assembly of VH and VL gene sequences in CDR-shuffling

| VL | VH | |
|---|---|---|
| Primer 759 | Primer 725 | 30 pmol |
| Primer 738 | Primer 729 | 0.6 pmol |
| Primer L2 | Primer H2 | 0.6 pmol |
| Primer L3 | Primer H3 | 0.6 pmol |
| Primer 745 | Primer 730 | 0.6 pmol |
| Primer L5 | Primer H5 | 0.6 pmol |
| Primer 744 | Primer 728 | 0.6 pmol |
| Primer 880 | Primer 727 | 30 pmol |
| Taq | Taq | 10 Units |
| dNTPs | dNTPs | 200 µM |
| 1× Taq buffer | 1× Taq buffer | to 100 µl |

Preheat 95° 10 minutes, 20 cycles: 95° 1 minutes, 68° 1 minutes, 72° 1 minutes 72° 10 minutes.

The VH and VL were then assembled into a scFv encoding sequence according to standard procedures (Griffiths et al 1994). The resulting library was subjected to panning so as to select binders with improved affinities to FITC. The selection procedure for the reshuffled library was essentially the same as for the initially shuffled library. The total number of clones obtained after selection was 510. Six clones (B) were chosen from this new pool and were tested and compared to 6 clones (A) from the first pool, originating from the shuffled library (Table 4).

TABLE 4

Dissociation-rates of individual clones selected from the shuffled library (clones A) and from the reshuffled library (clones B).

| Clone | $K_{DISS}$ (s$-1 \times 10^{-3}$) |
|---|---|
| scFv-B11 (original) | 12.9 |
| 1A | 6.3 |
| 12A | 5.7 |
| 13A | 9.0 |
| 14A | 9.7 |
| 16A | 1.8 |
| 17A | 7.9 |
| 22B | 0.2 |
| 31B | 0.3 |
| 32B | 9.8 |

TABLE 4-continued

Dissociation-rates of individual clones selected from the shuffled library (clones A) and from the reshuffled library (clones B).

| Clone | $K_{DISS}$ (s$-1 \times 10^{-3}$) |
|---|---|
| 33B | 6.8 |
| 34B | 7.3 |
| 35B | 8.7 |

Two clones from the reshuffling experiments (22B and 31B) exhibited substantially slower dissociation-rates, indicating that the reshuffling process yielded binders with improved affinities.

3. Cloning and Shuffling of Defined DNA Regions

Figure 6:
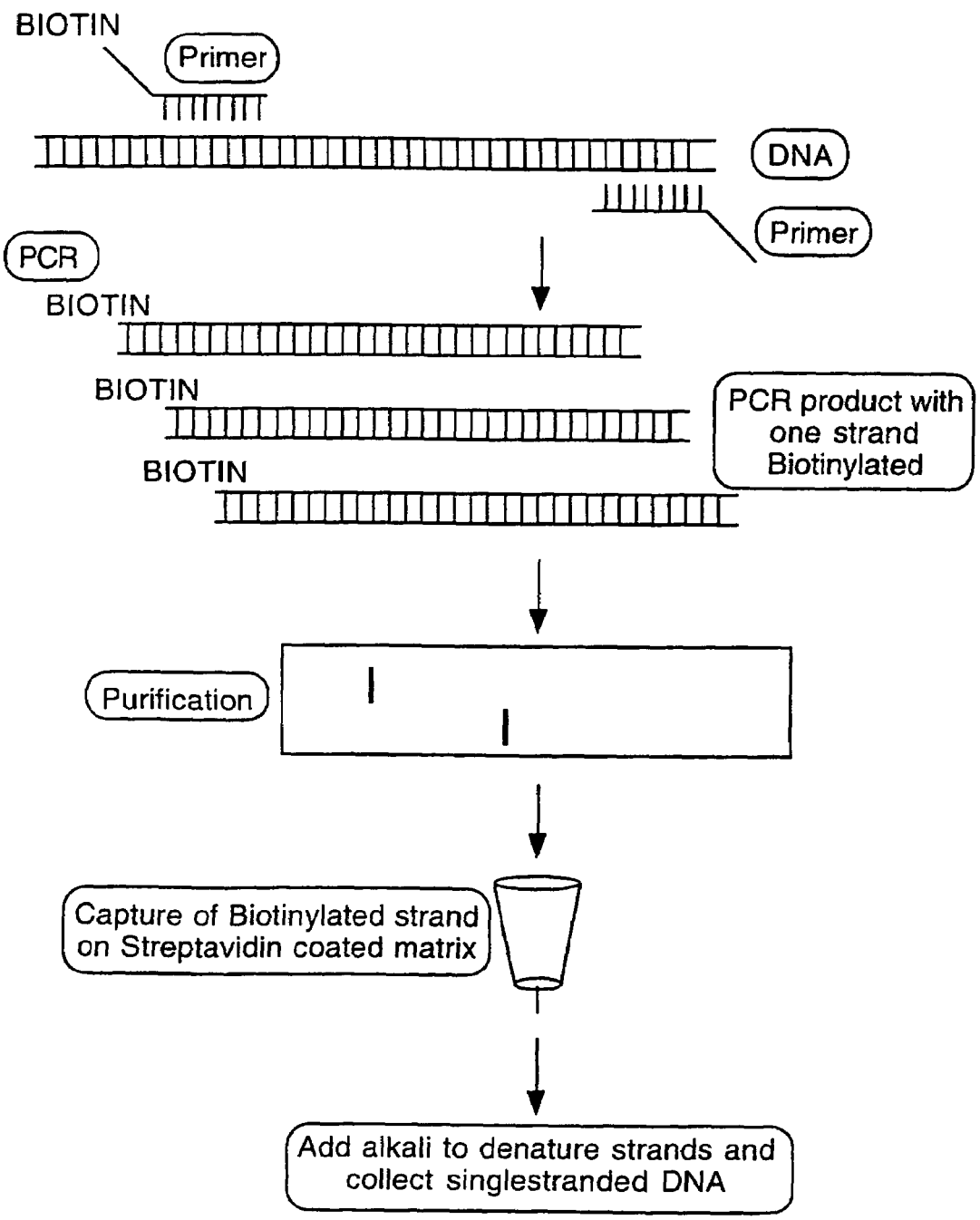
FIG. 6 shows the principles for the isolation of single-stranded DNA for the shuffling of defined DNA regions.

In our system it is possible to amplify defined regions from a cDNA library using two primers of which one is biotinylated. Using the biotin group, single stranded DNA can be isolated an used in the gene assembly process (FIG. 6). We have demonstrated this with the amplification of diverse CDR regions from an antibody gene library and the combination of these CDR regions randomly to a given framework region. Thus, defined regions of DNA (framework regions) can be interspaced by random regions of DNA (CDR regions) which have an in vivo orgin (Table 5). The CDR3 region vary in size (FIG. 7). Alternatively, these regions could be chemically synthesised.

TABLE 5

Combination of CDR regions from different germline sequences transplanted to the DP-47 framework encoding the variable heavy domain. For CDR1 and CDR2 the suggested germline origin is indicate. For CDR3 the number of residues in the CDR-region is written. N.D = not determined.

| Clone | CDR1 | CDR2 | CDR3 |
|---|---|---|---|
| 1 | DP-35 | DP-42 | 12 |
| 2 | DP-49 | DP-53 | 13 |
| 3 | N.D. | DP-51 | 11 |
| 4 | DP-32 | DP-47 | 10 |
| 5 | DP-41 | DP-47 | 8 |
| 6 | DP-32 | DP-77 | 9 |
| 7 | DP-31 | DP-47 | 7 |
| 8 | DP-49 | DP-35 | 5 |
| 9 | DP-49 | DP-35 | N.D. |
| 10 | DP-48 | DP-48 | N.D. |
| 11 | DP-51 | DP-47 | 10 |
| 12 | DP-34 | DP-31 | N.D. |
| 13 | DP-85 | DP-53 | 4 |
| 14 | DP-31 | DP-77 | 10 |
| 15 | DP-34 | DP-53 | 4 |

4. Library Construction.

Figure 8A:
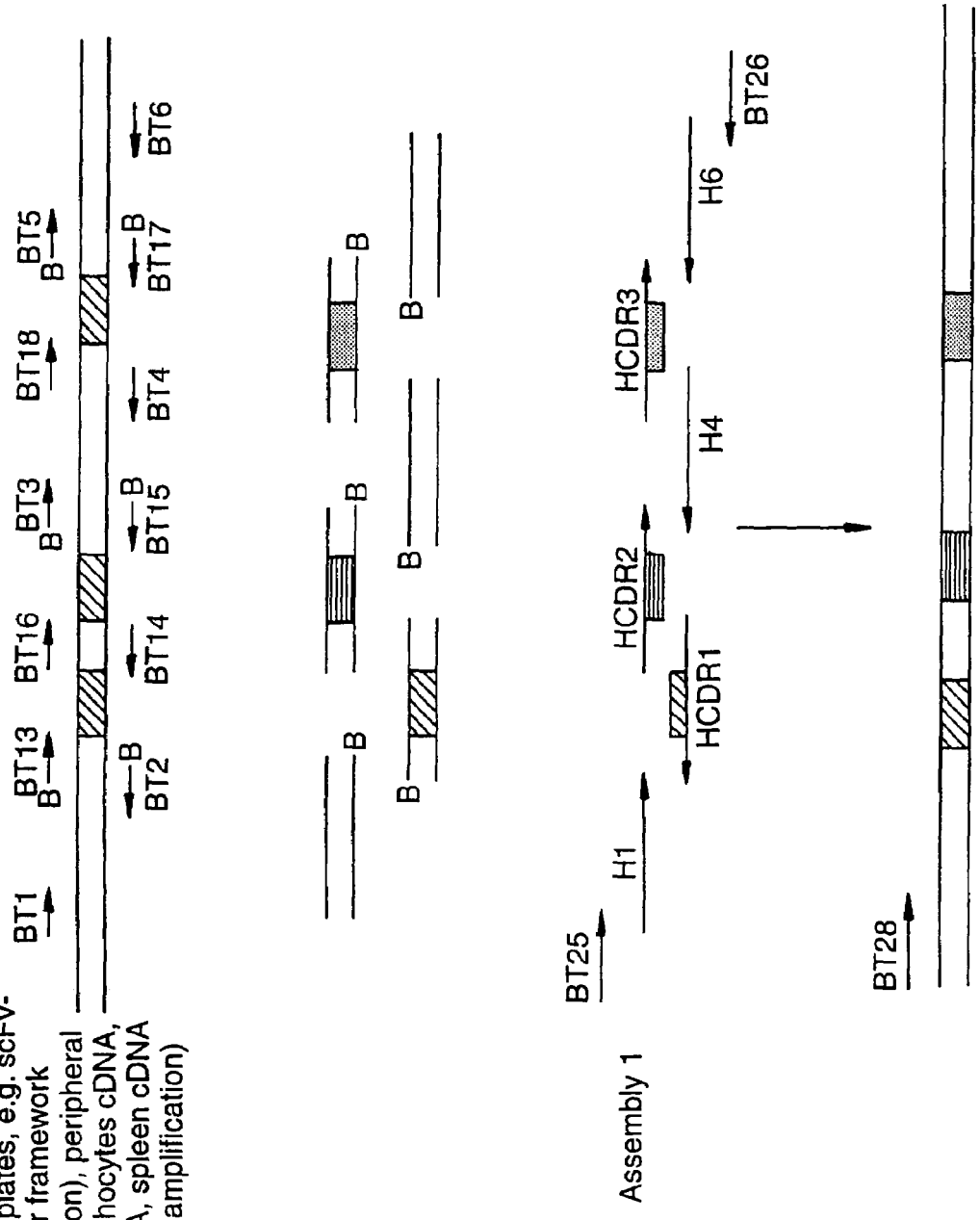
FIG. 8A: Assembly of genes for the VH-domain. The template for the framework region amplification is scFv-B11, whereas CDRs are amplified from cDNA prepared from peripheral blood lymphocytes, tonsils and spleen. An individual DNA fragment is amplified using two primers located at the ends of the fragments to be amplified and one of these primers is biotinylated at the 5' end. The individual DNA fragment is amplified and double-stranded DNA (dsDNA) is produced. This DNA is separated into two single stranded DNA molecules. The molecule without biotin is used in gene assembly, i.e. primers H1, H4, H6 and these primers contain no variation. Primers HCDR1, HCDR2, HCDR3 contain different CDR and are amplified using two primers adjacent to the particular CDR and one of these primers is biotinylated at the 5' end. The individual CDR is amplified and double-stranded DNA (dsDNA) is produced with the variation focused to the CDR since the two amplification primers do not contain any mutations. This DNA is separated into two singled stranded DNA molecules and used in gene assembly of VH domain in a library format, i.e. the variation in the CDRs is derived from different germ-line sequences. Primers BT25 and BT26 are synthesized in a DNA-synthesizing machine.

A gene library was constructed encoding scFv antibody fragments. The strategy used for this library is based on the assembly of a set of oligonucleotides into a sequence encoding VH and VL antibody domains (FIG. 8A, 8B.) Native in vivo formed CDR regions can be shuffled and assembled into a given master framework. In this example we have developed this concept further and assembled both VH and VL encoding gene sequences with native CDR regions into a given master framework. Thus, all-six CDR positions have been shuffled.

The template origin for CDR amplification was cDNA from peripheral blood B-cells, spleen, tonsills and lymphnodes. Oligonucleotides encoding the framework regions have also been amplified using the strategy with two flanking primers, where one is biotinylated (primers L1, H1 L4, H4, L6, H6). The primers used are described in Table 6 and in FIG. 8A, 8B.

TABLE 6

Sequences for primers used in library construction.
B = Biotin labeled 5' primer Amplification of framework fragments
BT1.  5' ACA GTC ATA ATG AAA TAC CTA TTG C 3'

BT2.  5' B-GC ACA GGA GAG TCT CA 3'

BT3.  5' B-CA CCA TCT CCA GAG ACA ATT CC 3'

BT4.  5' GGC CGT GTC CTC GGC TCT 3'

BT5.  5' B-TG GTC ACC GTG AGC AGC 3'

BT6.  5' CCG CCG GAT CCA CCT 3'

BT7.  5' CAG GCG GAG GTG GAT CCG GC 3'

BT8.  5' B-CG GGG GTC CCA GAC GCT 3'

BT9.  5' B-CG ATT CTC TGG CTC CAA GT 3'

BT10. 5' CTC ATC CTC GGA CCG GA 3'

BT11. 5' B-TC GGC GGA GGA ACC AAG CT 3'

BT12. 5' TGG CCT TGA TAT TCA CAA ACG AAT 3'

Amplification of in vivo CDR
BT13. 5' B-TC CCT GAG ACT CTC CTG TGC AGC CTC TGG ATT CAC CTT 3'

BT14. 5' TTC CCT GGA GCC TGG CGG ACC CA 3'

BT15. 5' B-GG AAT TGT CTC TGG AGA TGG TGA A 3'

BT16. 5' GTC CGC CAG GCT CCA 3'

BT17. 5' B-CG CTG CTC ACG GTG ACC AGT GTA CCT TGG CCC CA 3'

BT18. 5' AGA GCC GAG GAC ACG GCC GTG TAT TAC TGT 3'

BT19. 5' B-AG CGT CTG GGA CCC CCG GGC AGA GGG TCA CCA TCT CTT 3'

BT20. 5' GGG CCG TTC CTG GGA GCT GCT GAT ACC A 3'

BT21. 5' GCT CCC AGG AAC GGC CCC CAA ACT CCT CAT CTA T 3'

BT22. 5' B-GA CTT GGA GCC AGA GAA TCG GTC AGG GAC CCC 3'

BT23. 5' B-GT CAG CTT GGT TCC TCC GCC GAA 3'

BT24. 5' CTC CGG TCC GAG GAT GAG GCT GAT TAT TAC T 3'

Assembly of VH and VL
BT25. 5' B-TA CCT ATT GCC TAC GGC AGC CGC TGG ATT GTT ATT ACT CGC GGC CCA GCC GGC CAT GGC CGA 3'

BT26. 5' CCG CCG CAT CCA CCT CCG CCT GAA CCG CCT CCA CCG CTG CTC ACG GTG ACC A 3'

Amplification primers 2$^{nd}$ assembly
BT27. 5' B-TGG CCT TGA TAT TCA CAA ACG AAT 3'

BT28. 5' B-ACG GCA GCC GCT GGA TTG 3'

The PCR parameters for CDR and framework region amplification were essentially the same as described in example 2. The PCR parameters for assembly of genes encoding VH and VL are described in Table 7.

TABLE 7

PCR parameters for the assembly of VH and VL gene sequences for library construction.

| VH | VL | |
|---|---|---|
| Primer BT25 | Primer BT7 | 30 pmol |
| Primer H1 | Primer L1 | 0.6 pmol |
| Primer HCDR1 | Primer LCDR1 | 0.6 pmol |
| Primer HCDR2 | Primer LCDR2 | 0.6 pmol |
| Primer H4 | Primer L4 | 0.6 pmol |
| Primer HCDR5 | Primer LCDR3 | 0.6 pmol |
| Primer H6 | Primer L6 | 0.6 pmol |
| Primer BT26 | Primer BT12 | 30 pmol |
| Taq | Taq | 10 Units |
| dNTPs | dNTPs | 200 μM |
| 1× Taq buffer | 1× Taq buffer | to 100 μl |

Preheat 95° 10 minutes, 20 cycles: 95° 1 minutes, 68° 1 minutes, 72° 1 minutes and 72° 10 minutes.

The assembled VH and VL gene sequences were assembled into a scFv coding sequence using standard protocols (Griffiths et al 1994). A library of $1.1 \times 10^9$ members were constructed out of the 40 clones tested all 40 contained an insert of the right size as determined by PCR agarose gel electrophoresis. In order to test the variability in the library, PCR amplified and purified inserts were subjected to cleavage by BsTN1 and BamH1. Clones showed different restriction patterns, as determined by agarose gel electrophoresis and compared to the control scFv-B11 (FIG. 9).

In order to estimate the frequency of clones able to express scFv antibody fragments, clones from the library containing the FLAG sequence (Hopp et al, 1989), as well as control bacteria with and without FLAG sequence, were plated at low density on Luria broth-plates containing 100 μg/ml ampicillin, 25 μg/ml tetracycline and 1% glucose. The plates were grown at 37° C. over night and lifted to nitrocellulose filters by standard methods (Sambrook et al 1989). In order to induce synthesis of the scFv genes in the bacteria, filters were incubated for 4 hrs on plates containing 0.5 mM isopropyl-thio-β-D-galactoside (IPTG) but without glucose. Bacteria were then lysed by lyzosyme/chloroform treatment, the filters were washed and incubated with anti-FLAG M2 antibody (Kodak) followed by anti-mouse peroxidase conjugated second antibody (P260 Dakopatts) and detected by DAB 3,3'-diaminobenzidine tetrahydroklorid, Sigma) (Table 8).

TABLE 8

Frequency of intact antibody genes in the library

| Library Pool | Tested clones | FLAG positive clones | Percent positive clones |
|---|---|---|---|
| A | 145 | 88 | 60 |
| B | 77 | 52 | 67 |
| C | 158 | 105 | 66 |
| D | 68 | 48 | 70 |
| All library pools | 448 | 293 | 65.4 |
| Positive control pFAB5cHis scFvB11 | 64 | 64 | 100 |
| Negative control pFAB5cHis | 30 | 0 | 0 |

The anti-FLAG antibody detects a FLAG sequence situated downstream of the scFv gene in the library constructs as well as in the control vector pFAB5cHis scFvB11, but not in the original vector pFAB5cHis. Clones, to which the anti-FLAG antibody binds, therefore contains an intact open reading frame of the scFv gene.

REFERENCES

Barbas, C F et al: Proc Natl Acad Sci USA, 88:7978-82 (1991)
Barbas, C F et al: Proc Natl Acad Sci USA, 89:4457-61 (1992)
Crameri, A et al: Biotechniques, 18:194-196 (1995)
Griffiths, A D et al: EMBO J, 13:3245-3260 (1994)
Hoogenboom, H R et al: J Mol Biol, 227:381-8 (1992)
Hopp, T. P. et al: Biotechniques 7: 580-589 (1989)
Huse, W D et al: Science, 246:1275-81 (1989)
Larrick, J W et al: Biochem Biophys Res Commun, 160: 1250-6 (1989)
Leung, D W et al: Technique, 1:11-15 (1989)
Marks, J D et al: Biotechnology, 10:779-83 (1992)
McCafferty, J et al: Nature, 348:552-4 (1990)
Moore, J C et al: Nature Biotechnology, 14:458-467 (1996)
Parmley, S F et al: Gene, 73:305-318 (1988)
Roberts, S et al: Nature, 328:731-4 (1987)
Sambrook, J et al: Molecular cloning. A laboratory manual. Cold spring Harbor Laboratory Press 1989.
Stemmer, W P: Nature, 370:389-391 (1994)
Yang, W P et al: J Mol Biol, 254:392-403 (1995)

The invention claimed is:

1. A method of generating one or more assembled polynucleotide sequences encoding a protein of desired characteristics comprising the steps of:
   a) providing at least one polynucleotide sequence comprising one or more variant polynucleotide sequences encoding one or more variant protein motifs;
   b) providing one or more pairs of defined oligonucleotides, each pair representing spaced apart locations on the at least one polynucleotide sequence of step a) and each pair binding adjacent to a variant polynucleotide sequence encoding a variant protein motif from the at least one polynucleotide sequence of step a);
   c) using the pairs of defined oligonucleotides as amplification primers for PCR to amplify the variant polynucleotide sequences encoding the variant protein motifs of the at least one polynucleotide sequence of step a), performing PCR amplification on the at least one polynucleotide sequence of step a) and forming amplified polynucleotide sequences encoding the variant protein motifs;
   d) obtaining one or more single-stranded polynucleotide sequences from the amplified polynucleotide sequences in step c);
   e) providing one or more unmutated, specifically selected, scaffold polynucleotide sequences encoding one or more unmutated peptide regions from at least one polynucleotide sequence, wherein at least one polynucleotide sequence is different from the at least one polynucleotide sequence of step a); and
   f) annealing the polynucleotide sequences from step d) with the unmutated, specifically selected, scaffold sequences from step e) such that annealed polynucleotides with one or more gaps are formed, and filling the one or more gaps present in the annealed polynucleotides, thereby generating the one or more assembled polynucleotide sequences ecoding a protein of desired characteristics.

2. The method according to claim 1, wherein the at least one polynucleotide of step a) is subjected to error-prone PCR.

3. The method according to claim 1, wherein said PCR in step c) is error-prone PCR.

4. The method according to claim 1, wherein the oligonucleotides are single stranded.

5. The method according to claim 1, wherein one of said pairs of defined oligonucleotides is linked to a member of a specific binding pair (MSBP).

6. The method according to claim 5, further comprising the steps of isolating the amplified polynucleotide sequences encoding the variant protein motifs by binding the MSBP to its specific binding partner.

7. The method according to claim 5, wherein the MSBP is biotin.

8. The method according to claim 5, wherein the MSBP is streptavidin.

9. The method of claim 1, further comprising expressing the one or more assembled polynucleotide sequences to form expressed proteins.

10. The method according to claim 9, further comprising screening the expressed proteins for a protein having desired characteristics.

11. The method according to claim 10, further comprising selecting and expressing said protein having desired characteristics.

12. The method according to claim 1, wherein the at least one polynucleotide sequence of step a) encodes an antibody or antibody fragment capable of binding an antigen or other binding partner thereof.

13. The method of claim 12, wherein said one or more variant protein motifs are complementarity determining regions (CDRs).

14. The method according to claim 12, wherein the at least one polynucleotide sequence of step e) encodes an antibody or antibody fragment capable of binding an antigen or other binding partner thereof.

15. The method according to claim 14, wherein said antibody fragment is a single-chain variable fragment (scFv).

16. The method according to claim 14, wherein the one or more assembled polynucleotide sequences encode an antibodies or antibody fragments capable of binding an antigen or other binding partner thereof.

17. The method of claim 16, further comprising g) expressing said one or more assembled polynucleotide sequences to generate expressed proteins comprising said antibodies or antibody fragments.

18. The method of claim 17, further comprising h) screening the expressed proteins for ability to bind said antigen or other binding partner thereof, i) selecting one or more proteins having the greatest affinity for said antigen or other binding partner thereof from the expressed proteins, and, optionally, repeating steps a) through i) with the at least one polynucleotide sequence encoding said selected one or more proteins of step (i).

19. A method of creating a polynucleotide library encoding proteins comprising the steps of:
   a) providing at least one polynucleotide sequence comprising one or more variant polynucleotide sequences encoding one or more variant protein motifs;
   b) providing one or more pairs of defined oligonucleotides, each pair representing spaced apart locations on the at least one polynucleotide sequence of step a) and each pair binding adjacent to a variant polynucleotide sequence encoding a variant protein motif from the at least one polynucleotide sequence of step a);
   c) using the pairs of defined oligonucleotides as amplification primers for PCR to amplify the variant polynucleotide sequences encoding the variant protein motifs of the at least one polynucleotide sequence of step a), performing PCR amplification on the at least one polynucleotide sequence of step a) and forming amplified polynucleotide sequences encoding the variant protein motifs;
   d) obtaining one or more single-stranded polynucleotide sequences from the amplified polynucleotide sequences in step c);
   e) providing one or more unmutated, specifically selected, scaffold polynucleotide sequences encoding one or more unmutated scaffold peptide regions from at least one polynucleotide sequence, wherein at least one polynucleotide sequence is different from the at least one polynucleotide sequence of step a);
   f) annealing the polynucleotide sequences from step d) with the unmutated specifically selected, scaffold polynucleotide sequences from step e) such that annealed polynucleotides with one or more gaps are formed, and filling the one or more gaps present in the annealed polynucleotides, thereby generating one or more assembled polynucleotide sequences; and
   g) inserting said assembled polynucleotide sequences into suitable vectors, thereby creating said polynucleotide library encoding proteins.

20. The method according to claim 19, further comprising the step of expressing the proteins encoded by the polynucleotide library thereby generating a protein library.

21. The method according to claim 19, wherein the at least one polynucleotide of step a) is subjected to error-prone PCR.

22. The method according to claim 19, wherein said PCR in step c) is error-prone PCR.

23. The method according to claim 19, wherein the oligonucleotides are single stranded.

24. The method according to claim 19, wherein one of said pairs of defined oligonucleotides is linked to a member of a specific binding pair (MSBP).

25. The method according to claim 24, further comprising the steps of isolating the amplified polynucleotide sequences encoding the variant protein motifs by binding the MSBP to its specific binding partner.

26. The method according to claim 24, wherein the MSBP is biotin.

27. The method according to claim 24, wherein the MSBP is streptavidin.

28. The method according to claim 19, wherein the at least one polynucleotide sequence of step a) encodes an antibody or antibody fragment capable of binding an antigen or other binding partner thereof.

29. The method of claim 28, wherein said one or more variant protein motifs are complementarity determining regions (CDRs).

30. The method according to claim 28, wherein the at least one polynucleotide sequence of step e) encodes an antibody or antibody fragment capable of binding an antigen or other binding partner thereof.

31. The method according to claim 30, wherein said antibody fragment is a single-chain variable fragment (scFv).

32. The method according to claim 30, wherein the polynucleotide library encodes antibodies or antibody fragments capable of binding an antigen or other binding partner thereof.

33. The method of claim 32, further comprising h) expressing said polynucleotide library to generate expressed proteins comprising said antibodies or antibody fragments.

34. The method of claim 33, further comprising i) screening the expressed proteins for ability to bind said antigen or other binding partner thereof, j) selecting one or more proteins having the greatest affinity for said antigen or other binding partner thereof, from the expressed proteins, and, optionally, repeating steps a) through j) with the at least one polynucleotide sequence encoding said selected one or more proteins of step j).

* * * * *